(12) United States Patent
Wang et al.

(10) Patent No.: US 10,222,369 B2
(45) Date of Patent: Mar. 5, 2019

(54) METHODS FOR MAKING NOVEL ANTIGEN BINDING DOMAINS

(71) Applicant: Chimera Bioengineering, Inc., Menlo Park, CA (US)

(72) Inventors: Benjamin Wang, Menlo Park, CA (US); Gusti Zeiner, Pacifica, CA (US)

(73) Assignee: Chimera Bioengineering, Inc., Menlo Park, CA (US)

( * ) Notice: Subject to any disclaimer, the term of this patent is extended or adjusted under 35 U.S.C. 154(b) by 179 days.

(21) Appl. No.: 15/596,493

(22) Filed: May 16, 2017

(65) Prior Publication Data

US 2017/0336393 A1 Nov. 23, 2017

Related U.S. Application Data

(60) Provisional application No. 62/337,769, filed on May 17, 2016.

(51) Int. Cl.
| | |
|---|---|
| *C40B 30/04* | (2006.01) |
| *G01N 33/50* | (2006.01) |
| *C07K 14/725* | (2006.01) |
| *C07K 14/705* | (2006.01) |
| *C07K 16/28* | (2006.01) |
| *C07K 16/00* | (2006.01) |
| *C12N 15/85* | (2006.01) |

(52) U.S. Cl.
CPC ...... *G01N 33/5011* (2013.01); *C07K 14/7051* (2013.01); *C07K 14/70521* (2013.01); *C07K 16/005* (2013.01); *C07K 16/2887* (2013.01); *C07K 16/2896* (2013.01); *C12N 15/85* (2013.01); *G01N 33/502* (2013.01); *G01N 33/505* (2013.01); *G01N 33/5052* (2013.01); *C07K 2317/622* (2013.01); *C07K 2319/03* (2013.01); *C07K 2319/33* (2013.01); *C07K 2319/70* (2013.01); *C40B 30/04* (2013.01); *G01N 2500/10* (2013.01)

(58) Field of Classification Search
None
See application file for complete search history.

(56) References Cited

U.S. PATENT DOCUMENTS

| | | |
|---|---|---|
| 2010/0316609 A1 | 12/2010 | Dewhurst et al. |
| 2011/0003385 A1 | 1/2011 | Crabtree et al. |
| 2014/0120622 A1 | 5/2014 | Gregory et al. |

(Continued)

FOREIGN PATENT DOCUMENTS

| | | |
|---|---|---|
| WO | WO 2015/123642 | 8/2015 |
| WO | WO 2015/140268 | 9/2015 |

(Continued)

OTHER PUBLICATIONS

Jensen et al., Design and implementation of adoptive therapy with chimeric antigen receptor-modified T cells, 2013, Immunol Rev vol. 257, pp. 127-144.

(Continued)

*Primary Examiner* — Christian C Boesen
(74) *Attorney, Agent, or Firm* — HelixIP LLP

(57) ABSTRACT

The present invention relates generally to the field of making novel antigen binding domains against infectious diseases. The present invention also relates to novel CARs that utilize the novel antigen binding domains as an extracellular element. The present invention also relates to use of the novel antigen binding domains as therapeutic agents.

20 Claims, 3 Drawing Sheets

(56) References Cited

U.S. PATENT DOCUMENTS

| | | |
|---|---|---|
| 2014/0242701 A1 | 8/2014 | Shiku et al. |
| 2014/0271583 A1 | 9/2014 | Allen-Hoffmann et al. |
| 2014/0286987 A1 | 9/2014 | Spencer et al. |
| 2014/0349402 A1 | 11/2014 | Cooper et al. |

FOREIGN PATENT DOCUMENTS

| | | |
|---|---|---|
| WO | WO 2015/142675 | 9/2015 |
| WO | WO 2015/193406 | 12/2015 |
| WO | WO2016/028896 | 2/2016 |
| WO | WO 2016/028896 | 2/2016 |

OTHER PUBLICATIONS

Kloss et al., Combinatorial antigen recognition with balanced signaling promotes selective tumor eradication by engineered T cells, 2013, Nat Biotechnol vol. 31, pp. 71-75.

Lienert et al., Synthetic biology in mammalian cells: Next generation research tools and therapeutics, 2014, Natl Rev Molc Cell Biol vol. 15, pp. 95-107.

Adusumilli et al., Regional Delivery of Mesothelin-Targeted CAR T-cell Therapy Generates Potent . . . Tumor Immunity, Nov. 2014, Sci. Transl. Med. 6:261ra151.

Aranda et al., Adoptive Cell Transfer for Anticancer Immunotherapy, Apr. 2015, OncoImmunol. 3:5, e28344.

Auslander, et al., From Gene Switches to Mammalian Designer Cells: Present and Future Prospects, Mar. 2013, Trends Biotechnol. 31:155-168.

Baker et al., Structural and Dynamic Control of T-cell Receptor Specificity, Cross-Reactivity, and Binding Mechanism, 2012, Immunol. Rev. 250:10-31.

Beilstein, et al., Conditional Control of Mammalian Gene Expression by Tetracycline-Dependent Hammerhead Ribozymes, Sep. 2014, Synth. Biol. 4:526-534.

Berens, et al., RNA Aptamers as Genetic Control Devices: The Potential of Riboswitches as Synthetic Elements for Regulating Gene Expression, 2015, Biotechnol. 10:246-257.

Bonifant, et al., Toxicity and Management in CAR T-cell Therapy, 2016, Oncolytics 3:16011.

Bray, et al., On-Site AR Parking, 2015, Sci. Transl. Med. 7:275ra22.

Brayer et al., Developing Strategies in the Immunotherapy of Leukemias, Jan. 2013, Cancer Control 20:49-59.

Brentjens, et al., Adoptive Therapy of Cancer with T cells Genetically Targeted to Tumor Associated Antigens Through . . . , May 2011, Am Soc Gene Cell Therap., presentation.

Brudno et al., Allogenic T Cells That Express and Anti-CD19 Chimeric Antigen Receptor Induce Remissions of B-cell . . . , 2016, Am Soc Clin Oncol 34.

Buckley et al., Update on Antigen-Specific Immunotherapy of Acute Myeloid Leukemia, 2015, Curr. Hematol. Malig. Rep. 10:65-75.

Budde et al., Combining a CD20 Chimeric Antigen Receptor and an Inducible Caspace 9 Suicide Switch to Improve the Efficacy . . . , Dec. 2013, PLoS ONE 8:e82742.

Cantelmo, et al., Inhibition of the Glycolytic Activator PFKFB3 in Endothelium Induces Tumor Vessel Normalization . . . , Dec. 2016, Cancer Cell 30:968-985.

Caruso et al., Tuning Sensitivity of Car to EGFR Density Limits Recognition of Normal Tissue While Maintaining . . . , 2015, Cancer Res. 75:3505-3518.

Chakravarti et al., Synthetic Biology in Cell-Based Cancer Immunotherapy, 2015, Trends Biotechnol. 33:449-461.

Chang et al., Posttranscriptional Control of T Cell Effector Function by Aerobic Glycolysis, Jun. 2013, Cell 153:1239-1251.

Chang et al., Identification and Selective Expansion of Functionally Superior T cells Expressing Chimeric Antigen Receptors, 2015, J. Transl. Med. 13:161.

Cheadle et al., CAR T cells: Driving the Road from the Laboratory to the Clinic, 2013, Immunol. Rev. 257:91-106.

Chen et al., Genetic Control of Mammalian T-cell Proliferation with Synthetic RNA Regulatory Systems, 2010, Proc. Natl Acad. Sci. 107:8531-8536.

Chen et al., Efficient Gene Editing in Primary Human T cells, Nov. 2015, Trends Immunol. 36:667-669.

Cooper et al., Moving from Tinkering in the Garage to Assembly Line Production: the Manufacture of Genetically Modified T cells . . . , 2015, Cancer Gene Therap. 22:64-66.

Darcy et al., Adoptive Immnotherapy: a New Era for the Treatment of Cancer, 2015, Immunotherap. 7:469-471.

Davila et al., Efficacy and Toxicity Management of 19-28z CAR T cell Therapy in B cell Acute Lymphoblastic Leukemia, Feb. 2014, Sci Transl Med 6:224ra25.

Di Stasi et al., Inducible Apoptosis as a Safety Switch for Adoptive Cell Therapy, 2011, N. Engl. J. Med. 265:1673-83.

Dotti et al., Design and Development of Therapies Using Chimeric Antigen Receptor-Expressing T cells, Jan. 2014, Immunol. Rev. 257:107-126.

Elert et al., Calling Cells to Arms, Dec. 2013, Nature 504:S2-S3.

Elfakess et al., Unique Translation Initiation of mRNAs-Containing TISU Element, Jun. 2011, Nucl. Acids. Res. 39:7598-7609.

Ellebrecht et al., Reengineering Chimeric Antigen Receptor T cells for Targeted Therapy of Autoimmune Disease, Jul. 2016, Science 353:179-184.

Farajnia et al., Development Trends for Generation of Single-Chain Antibody Fragments, Aug. 2014, Immunopharmacol. Immunotoxicol. 36:297-308.

Federov et al., PD-1 and CTLA-4 Based Inhibitory Chimeric Antigen Receptors (iCARs) Divert Off-Target Immunotherapy . . . , Dec. 2013, Sci. Transl. Med. 5:215ra172.

Festuccia et al., Allogenic Stem Cell Transplantation in Multiple Myeloma: Immunotherapy and New Drugs, Jun. 2015, Expert Opin. Biol. Therapy 15:857-872.

Garber et al., Adoptive T-cell Therapy for Leukemia, 2014, Molc. Cell. Therap. 2:25-.

Garcia-Sanz et al., Translational Control: a General Mechanism for Gene Regulation During T cell Activation, 1998, FASEB J. 12:299-306.

Ghorashian et al., CD19 Chimeric Antigen Receptor T cell Therapy for Haematological Malignancies, Mar. 2015, Brit, J. Haematol. 169:463-478.

Grada et al., TanCAR: A Novel Bispecific Chimeric Antigen Receptor for Cancer Immunotherapy, 2013, Molc. Therap. Nucl. Acids 2:e105.

Hamilton et al., Delineation of a Novel Pathway that Regulates CD154 (CD40 Ligand) Expression, 2003, Molc. Cell. Biol. 23:510-525.

Hjelm et al., Mifepristone-Inducible Transgene Expression in Neural Progenitor Cells in vitro and in vivo, 2016, Gene Therap. 23:424-437.

Horton et al., Recent Advances in Acute Myeloid Leukemia Stem Cell Biology, 2012, Haematolog. 97:966-974.

Huang et al., Driving an Improved CAR for Cancer Immunotherpy, 2016, J. Clin. Invest. 126:2795-2798.

Hudecek et al., The Nonsignaling Extracellular Spacer Domain of Chimeric Antigen Receptors is Decisive for In Vivo . . . , Sep. 2014, Cancer Immunol. Res. 3:125-135.

Hurton et al., Tethered IL-15 Augments Antitumor Activity and Promotes a Stem-Cell Memory Subset in Tumor-Specific T cells, Nov. 2016, Proc. Natl Acad Sci 113:E7788-E7797.

Hussaini et al., Targeting CD123 in AML Using a T-cell Directed Dual-Affinity Re-Targeting (DART) Platform, Nov. 2015, Blood 127:122-131.

Iwamoto et al., A General Chemical Method to Regulate Protein Stability in the Mammalian Central Nervous System, 2010, Chem Biol 17:981-988.

Jensen et al., Enhancing the IQ of CAR Modified T Cells, 2015, Powerpoint Slides.

Jensen et al., Mathematical Modeling of Chimeric TCR Triggering Predicts the Magnitude of target Lysis and its Impairment by TCR . . . , 2010, J. Immunol. 184:4284-4294.

(56) References Cited

OTHER PUBLICATIONS

Jensen et al., Design and Implementation of Adoptive Therapy with Chimeric Antigen Receptor-Modified T cells, 2014, Immunol. Rev. 257:127-144.
Jensen, Synthetic Immunobiology Boosts the IQ of T cells, Oct. 2015, Science 350:514-515.
Jensen et al., Designing Chimeric Antigen Receptors to Effectively and Safely Target Tumors, 2015, Curr. Opin. Immunol. 33:9-15.
Johnson et al., Rational Development and Characterization of Humanized Anti-EGFR Variant III Chimeric Antigen Receptor . . . , Feb. 2015, Sci. Transl. Med. 7:275ra22.
Juillerat et al., Design of Chimeric Antigen Receptors with Intergrated Controllable Transient Functions, 2016, Sci. Rep. 6:18950.
June, Drugging the Undruggable Ras—Immunotherapy to the Rescue? 2016, N. Eng. J. Med. 375:2286-2289.
Kakarla et al., CAR T cells for Solid Tumors: Armed and Ready to Go? Mar.-Apr. 2014, Cancer J. 20:151-155.
Kalos et al., Adoptive T cell Transfer for Cancer Immunotherapy in the Era of Synthetic Biology, Jul. 2013, Immunity 39:49-60.
Kawalekar et al., Distinct Signaling of Coreceptors Regulates Specific Metabolism Pathways and Impacts Memory Development . . . , 2016, Immunity 44:380-390.
Kebriaei et al., Future of Therapy in Acute Lymphoblastic Leukemia (ALL)—Potential Role of Immune-Based Therapies, 2015, Curr. Hematol. Malig. Rep. 10:76-85.
Kebriaei et al., Phase I Trials Using Sleeping Beuaty to Generate CD19-Specific CAR T cells, 2016, J. Clin. Invest. 126:3363-3376.
Kershaw et al., Clinical Application of Genetically Modified T cells in Cancer Therapy, May 2014, Clin. Transl. Immunol. 3:e16.
Kim et al., Highly Efficient RNA-Guided Genome Editing in Human Cells Via Delivery of Purified Cas9 Ribonucleoproteins, Jun. 2014, Gen. Res. 24:1012-1019.
Kis et al., Mammalian Synthetic Biology: Emerging Medical Applications, Mar. 2015, J. R. Soc. Interface 12:20141000.
Kochenderfer et al., Chemotherapy-Refractory Diffuse Large B-cell Lymphoma and Indolent B-cell Malignancies can be Effectively . . . , Aug. 2014, J. Clin. Oncol. 33:540-549.
Ledford, T-cell Therapy Extends Cancer Survival to Years, Dec. 2015, Nature 516:156.
Liang et al., Engineering Biological Systems with Synthetic RNA Molecules, 2011, Molc. Cell 43:915-926.
Lynn et al., Targeting of Folate Receptor-beta on Acute Myeloid Leukemia Blasts with Chimeric Antigen Receptor-Expressing T cells, May 2015, Blood 125:3466-3476.
Lindsten et al., Regulation of Lymphokine Messenger RNA Stability by a Surface-Mediated T Cell Activation Pathway, 1989, Science 244:339-343.
Liu et al., Affinity Tuned ErbB2 or EGFR Chimeric Antigen Receptor T Cells Exhibit an Increased Therapeutic Index Against Tumors in Mice, Sep. 2015, Cancer Res. 75:3596-3607.
Long et al., 4-1BB Cotimulation Ameliorates T cell Exhaustion Induced by Tonic Signaling of Chimeric Antigen Receptors, Jun. 2015, Nat Med 21:581-590.
Marcus et al., Allogenic Chimeric Antigen Receptor-Modified Cells for Adoptive Cell Therapy of Cancer, Mar. 2014, Expert Opin Biol Therap 14:947-954.
Mardiros et al., T cells Expressing CD123-Specific Chimeric Antigen Receptors Exhibit Specific Cytolytic Effector Functions . . . , Sep. 2013, Blood 122:3138-3148.
Maude et al., Chimeric Antigen Receptor T cells for Sustained Remissions in Leukemia, Mar. 2014, N. Eng. J. Med. 371:1507-1517.
Maus et al., Antibody-Modified T cells: CARs Take the Front Seat for Hematologic Malignancies, Apr. 2014, Blood 123:2625-2635.
Mayer, Nucleic Acid Aptamers: Selection, Characterization and Application, 2016, Humana Press, Springer Science.
Morgan et al., Case Report of a Serious Adverse Event Following the Administration of T cells Transduced with a Chimeric Antigen Receptor . . . , 2010, Molc Therap 18:843-851.
Nagy et al., Glyceraldehyde-3-phosphate Dehydrogenase Selectively Binds AU-Rich RNA in the NAD+-Binding Region, 1995, J Biol Chem 270:2755-2763.
Nelson et al., Novel Immunotherapies for Hematologic Malignancies, Jan. 2015, Immunol. Rev. 263:90-105.
Newick et al., CAR T cell Therapy for Solid Tumors, Jul. 2016, Ann. Rev. Med. 68:3.1-3.14.
Norelli et al., Clinical Pharmacology of CAR-T cells: Linking Cellular Pharmacodynamics to Pharmacokinetics and Antitumor Effects, 2016, Biochim Biophys Acta 1865:90-100.
Okoye et al., The Protein LEM Promotes CD8+ T cell Immunity Through Effects on Mitochondrial Respiration, May 2015, Science 348:995-1001.
Paszkiewicz et al., Targeted Antibody-Mediated Depletion of Murine CD19 CAR T cells Permanently Reverses B cell Aplasia, 2016, J Clin Ivest 126:4262-4272.
Perales-Puchalt et al., Follicle-Stimulating Hormone Receptor is Expressed by Most Ovarian Cancer Subtypes and is a Safe . . . , 2016, Clin. Cancer Res.
Pizzitola et al., Chimeric Antigen Receptors Against CD33/CD123 Antigens Efficiently Target Primary Acute Myeloid Leukemia Cells in vivo, Aug. 2014, Leukemia 28:1596-1605.
Poirot et al., Multiplex Genome-Edited T-cell Manufacturing Platform for "Off-the-Shelf" Adoptive T-cell Immunotherapies, 2015, Cancer Res 75:3853-3864.
Posey et al., Engineered CAR T cells Targeting the Cancer-Associated Tn-Glycoform of the Membrane Mucin MUC1 Control Adenocarcinoma, 2016, Immunity 44:1444-1454.
Qin et al., Systematic Comparison of Constitutive Promoters and the Doxycycline-Inducible Promoter, 2010, PLoS ONE 5:e10611.
Rakhit et al., Chemical Biology Strategies for Posttranslational Control of Protein Function, Sep. 2014, Chem Biol 21:1238-1252.
Reddy, Changing Landscape of Immuno-Oncology: CAR-T Therapy and PD1/PDL1 Blockade, 2016, Boston University Theses.
Renert, Novel Immunotherapeutic Approaches to the Treatment of Cancer: Drug Development and Clinical Application, 2016, Springer International Publishing.
Rodgers et al., Switch-Mediated Activation and Retargeting of CAR-T cells for B-cell Malignancies, 2016, Proc Natl Acad Sci 113:E459-E468.
Rosenberg, Cell Transfer Immunotherapy for Metastataic Solid Cancer—What Clinicians Need to Know, 2011, Nat Rev Clin Oncol 8:577-585.
Rosenberg et al., Adoptive Cell Transfer as Personalized Immunotherapy for Human Cancer, Apr. 2015, Science 348:62-68.
Roybal et al., Precision Tumor Recognition by T cells with Combinatorial Antigen-Sensing Circuits, 2016, Cell 164:770-779.
Roybal et al., Engineering T cells with Customized Therapeutic Response Programs Using Synthetic Notch Receptors, 2016, Cell 167:1-14.
Sadelain et al., Sage Harbours for the Integration of New DNA in the Human Genome, 2012, Nat. Rev. 12:51-58.
Sandberg et al., In Cancer Immunotherapy Legal Battle, It's Now Juno v. Novartis, Feb. 2014, Pharma MedTech Bus Intell. 2014900027.
Shi et al., Chimeric Antigen Receptor for Adoptive Immunotherapy of Cancer: Latest Research and Future Prospects, Sep. 2014, Molc Cancer 13:219.
Sommermeyer et al., Chimeric Antigen Receptor-Modified T cells Derived from Defined CD8+ and CD4+ Subsets Confer Superior Antitumor . . . , Feb. 2016 Leukemia 30:492-500.
Srivastava et al., Engineering CAR-T cells: Design Concepts, Aug. 2015, Trends Immunol 36:494-502.
Sun et al., The Quest for Spatio-Temporal Control of CAR T cells, Dec. 2015, Cell Res. 25:1281-1282.
Tettamanti et al., CD123 AML Targeting by Chimeric Antigen Receptors: A Novel Magic Bullet for AML Therapeutics? May 2014, Oncolimmunol 3:e28835.
Till et al., Adoptive Immunotherapy for Idolent Non-Hodgkin Lymphoma and Mantle Cell Lymphoma Using Genetically Modified . . . , 2008, Blood 112:2261-2271.
Turatti et al., Redirected Activity of Human Antitumor Chimeric Immune Receptors is Governed by Antigen and Receptor Expression Levels . . . , 2007, J Immunotherap 30:684-693.

(56) References Cited

OTHER PUBLICATIONS

Turtle et al., CD19 CAR-T cells of Defined CD4+:CD8+ Composition in Adult B cell ALL Patients, 2016, J Clin Ivest 126:2123-2138.
Turtle et al., Immunotherapy of Non-Hodgkin's Lymphoma with a Defined Ratio of CD8+and CD4+ CD19-Specific Chimeric Antigen Receptor . . . , 2016, Sci Transl Med 8:355ra116.
Vanderlugt et al., Epitope Spreading in Immune-Mediated Diseases: Implications for Immunotherapy, 2002, Nat Rev 2:85-95.
Vigano et al., Functional Avidity: a Measure to Predict the Efficacy of Effector T cells? 2012, Clin Develop Immunol 2012:153863.
Wang et al., ZAP-70: An Essential Kinase in T-cell Signaling, 2010, Cold Spring Barb Perspect Biol 2:a002279.
Wang et al., One-Step Generation of Mice Carrying Mutations in Multiple Genes by CRISPR/Cas-Mediated Genome Engineering, 2013, Cell 153:910-918.
Wang et al., Manufacture of tumor- and virus-specific T lymphocytes for adoptive cell therapies, Feb. 2015, Cancer Gene Therapy 22:85-94.
Watanabe et al., Target Antigen Density Governs the Efficacy of Anti-CD20-CD28-CD3 Zeta Chimeric Antigen Receptor-Modified . . . , Dec. 2014, J Immunol 194:911-920.
Weigand et al., Tetracycline Aptamer-Controlled Regulation of Pre-mRNA Splicing in Yeast, 2007, Nucl Acids Res 35:4179-4185.
Win et al., A Modular and Extensible RNA-Based Gene-Regulatory Platform for Engineering Cellular Function, 2007, Proc Natl Acad Sci 104:14283-14288.
Win et al., Frameworks for Programming Biological Function Through RNA Parts and Devices, 2009, Chem Biol 16:298-310.
Wu et al., Remote Control of Therapeutic T cells Through a Small Molecule-Gated Chimeric Receptor, Sep. 2015, Science 350:aab4077.
Xie et al., Mammalian Designer Cells: Engineering Principles and Biomedical Applications, Jul. 2015, Biotechnol J 10:1005-1018.
Xie et al., Synthetic Biology—Application-Oriented Cell Engineering, 2016, Curr. Opin. Biotechnol. 40:139-148.
Ye et al., Synthetic Mammalian Gene Circuits for Biomedical Applications, 2013, Curr. Opin. Chem Biol 17:910-917.
Zhao et al., Structural Design of Engineered Costimulation Determines Tumor Rejection Kinetics and Persistence of CAR T cells, Oct. 2015, Cancer Cell 28:415-428.
Zheng et al., Protein L: A Novel Reagent for the Detection of Chimeric Antigen Receptor (CAR) Expression by Flow Cytometry, 2012, J Transl Med 10:29.
Muti, ASH Conference Review, 2014.
Zhong et al., Rational Design of Aptazyme Riboswitches for Efficient Control of Gene Expression in Mammalian Cells, Nov. 2016, eLife 5:e18858.
Auslander et al., A ligand-dependent hammerhead ribozyme switch for controlling mammalian gene expression, Molc. Biosys. vol. 6, pp. 807-814 (2010).
Rakhit et al., Evaluation of FKBP and DHFR based destabilization domains in *Sacchromyces cerevisiae*, 2011, Bioorg Med Chem Lett vol. 21, pp. 4965-4968.
Iwamoto et al., A general chemical method to regulate protein stability in the mammalian nervous system, 2010, Chem & Biol vol. 17, pp. 981-988.
Rakhit et al., Evaluation of FKBP and DHFR based destabilizing domains in *Sacchromyces cerevisiae*, 2011, Bioorg. Med Chem Lett vol. 21, pp. 4965-4968.

METHODS FOR MAKING NOVEL ANTIGEN BINDING DOMAINS

This application claims the benefit of provisional application Ser. No. 62/337,769 filed on May 17, 2016.

BACKGROUND OF THE INVENTION

When a new infectious disease enters a population it can create a pandemic in which a large number of individual in the population become infected with the disease. In part, the disease rate may be high because the subjects in the population have not had prior exposure to the new infectious agent. Recent pandemics include, for example, the world wide 2009 H1N1 flu outbreak, the 2014 Ebola outbreak in Western Africa, and the world wide HIV outbreak from the 1980's to present. During disease outbreaks some subjects in a population may develop immunity against the infectious disease while others do not and non-immune subjects may succumb to the disease.

Chimeric Antigen Receptors are human engineered receptors that may direct a T-cell to attack a target recognized by the CAR. For example, CAR T cell therapy has been shown to be effective at inducing complete responses against acute lymphoblastic leukemia and other B-cell-related malignancies and has been shown to be effective at achieving and sustaining remissions for refractory/relapsed acute lymphoblastic leukemia (Maude et al., NEJM, 371:1507, 2014). CARs include an antigen binding domain that is engineered into the man made receptor to target the CAR to an antigen of choice.

It is an object of the invention to use CAR constructs to find novel antigen binding domains for treating diseases such as cancer, infectious diseases, or aging-related conditions. It is also an object of the invention to make novel CARs using these novel antigen binding domains. It is an object of the invention to make novel antigen binding proteins that can be used as therapeutics against a disease.

SUMMARY OF THE INVENTION

In some embodiments, the invention relates to methods for finding new antigen binding domains against antigens associated with a disease. In some embodiments, the invention relates to methods for finding new antigen binding domains against antigens newly associated with a disease. In some embodiments, the invention relates to identifying new target antigens and antigen binding domain pairs. In some embodiments, the invention related to validating new antigen targets for a disease or condition. In some embodiments, the invention is used to find antigen binding domains that bind antigens associated with an infectious disease. In some embodiments, antigen binding domains are obtained from a subject who has become immune to the infectious disease. In some embodiments, the invention is used to find antigen binding domains that bind antigens associated with a cancer. In some embodiments, the invention is used to find self-antigen binding domains associated with autoimmune diseases. In some embodiments, antigen binding domains are obtained from a subject whose immune system has responded to an antigen. In some embodiments, the antigen binding domain is from an antibody. In some embodiments, the antigen binding domain is from a T-cell receptor. In some embodiments, the antigen binding domain is from a receptor such as, for example the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105). In some embodiments, the antigen binding domains are obtained from the lymphocytes of a subject exposed to the antigen. In some embodiments, potential antigen binding domains are engineered into a CAR construct to be screened for activity against a target antigen.

In some embodiments, the invention relates to CAR, Smart-CAR, DE-CAR, and/or Side-CAR constructs that do not have an extracellular element (an antigen binding domain) for use in the invention. These partial CAR constructs are called CAR chassis, and can be combined with antigen binding domains obtained from a subject to make a library of CAR constructs with potential antigen binding domains for the disease antigen. In some embodiments, the CAR chassis constructs comprise a nucleic acid encoding a CAR (chimeric antigen receptor) chassis with a nucleic acid encoding a Destabilizing Element or a nucleic acid encoding a RNA control device. In some embodiments, the invention relates to CAR chassis, Smart CAR chassis, DE-CAR chassis, and/or Smart-DE-CAR chassis that are comprised of at least two parts which associate to form a CAR chassis, Smart CAR chassis, DE-CAR chassis and/or Smart-DE-CAR chassis of the invention (called Side-CAR chassis). In some embodiments, the chassis are combined with an antigen binding domain to form CAR, Smart CAR, DE-CAR, Smart-DE-CAR, and/or Side CAR constructs. In some embodiments, a library of antigen binding elements are combined with the chassis for a CAR, Smart CAR, DE-CAR, Smart-DE-CAR, and/or Side CAR and a library of CAR, Smart CAR, DE-CAR, Smart-DE-CAR, and/or Side CAR constructs are made.

In some embodiments, novel antigen binding domains are obtained from subjects who have become immune to an infectious agent. In some embodiments, novel antigen binding domains are obtained from subjects who have become immune to a cancer, infectious disease, or other immunologic challenge. In some embodiments, novel antigen binding domains are obtained from subjects who have been challenged with an antigen. In some embodiments, novel antigen binding domains are obtained from subjects who have had an immune response to a cancer, infectious disease, or other immunologic challenge. In some embodiments, immune cells from the subject are obtained and nucleic acids encoding antigen binding proteins are obtained from the immune cells. In some embodiments, nucleic acids encoding the antigen binding proteins are antibodies and are obtained from, for example, plasma cells and memory B-cells. In some embodiments, the nucleic acids encoding the antigen binding proteins are T-cell receptors from, for example, cytotoxic T-cells, helper T-cells, and memory T-cells.

In some embodiments, the nucleic acids obtained from a subject are used to make a library of nucleic acids encoding antigen binding domains. In some embodiments, the nucleic acids encode antibody heavy and light chains from a subject or other source (including, for example, synthetic sources). In some embodiments, the nucleic acids represent the immune antibody repertoire of a subject who has become immune to an infectious disease, cancer, or other immunogenic challenge. In some embodiments, the nucleic acids represent the antibody repertoire of a subject who has had an immune response to an infectious disease, cancer, or other immunogenic challenge. In some embodiments, the antibody repertoire is from a subject that is naïve for the target antigen. In some embodiments, the antibody repertoire represents the germ line repertoire of a subject or species. In some embodiments, the nucleic acids encoding the heavy and light chains of the antibody are combined in a combinatorial fashion to generate many different combinations of light chains and heavy chain. In some embodiments, the nucleic acids represent the T-cell receptor repertoire of a subject who has become immune to an infectious disease, cancer, or other immunogenic challenge. In some embodiments, the nucleic acids represent the T-cell receptor repertoire of a subject who has had an immune reaction to an infectious disease, cancer, or other immunogenic challenge. In some embodiments, the T-cell receptor repertoire is from a subject that is naïve for the target antigen. In some embodiments, the T-cell receptor repertoire represents the germ line repertoire of a subject or species. In some embodiments, the nucleic acids encoding the alpha, beta, gamma and zeta chains of the T-cell receptor are combined in appropriate combinatorial fashion to generate a repertoire of antigen binding domains from the T-cell receptor chains.

In some embodiments, the nucleic acids encoding the antigen binding domains are engineered into single chain molecules, and these nucleic acids are operably linked to CAR chassis, Smart CAR chassis, DE-CAR chassis, Smart-DE-CAR chassis, and/or Side CAR chassis of the invention. In some embodiments, antigen binding domains that bind to target antigens can be screened or selected for from the CAR, Smart CAR, DE-CAR, Smart-DE-CAR, and/or Side CAR constructs with the candidate antigen binding domains. In some embodiments, the CAR, Smart CAR, DE-CAR, Smart-DE-CAR, and/or Side CAR constructs that bind to target antigens can be used in therapeutic applications.

In some embodiments, the target antigen of the new antigen binding domains is validated. In some embodiments, the antigen binding domain is used to identify and validate the target antigen. In some embodiments, the target antigen is associated with a cancer cell. In some embodiments, the target antigen is associated with an infectious disease. In some embodiments, the antigen binding domain is used to purify the target antigen by immunoaffinity. In some embodiments, a CAR, Smart CAR, DE-CAR, Smart-DE-CAR, and/or Side CAR construct with the antigen binding domain is used to identify the target antigen. In some embodiments, cancer cells, cells infected with an infectious agent, and/or infectious agents are disrupted and the disrupted materials are subjected to purification techniques. In some embodiments, the purification technique uses the antigen binding domain. In some embodiments, the target antigen is isolated by immune precipitation with the antigen binding domain. In some embodiments, a column with the antigen binding domain is used to affinity purify the target antigen. In some embodiments, purification fractions are tested using the antigen binding domains to identify fractions with target antigen.

In some embodiments, the Smart CAR, DE-CAR, Smart-DE-CAR, and/or Side-CAR nucleic acids of the invention are placed into an expression vector suitable for expression in a eukaryotic cell. In some embodiments, the nucleic acid is a DNA or RNA. In some embodiments, the RNA control device, DE, and/or Side CAR are used to control expression of the CAR in the eukaryotic cell. In some embodiments, the inducible expression of the CAR, Smart CAR, DE-CAR, Smart-DE-CAR, and/or Side CAR is used as a control in the screening or selection for antigen binding domains that bind to target antigen. In some embodiments, inducible control is used to verify that the growth and/or reporter signal detected is due to the particular CAR, Smart CAR, DE-CAR, Smart-DE-CAR, and/or Side CAR construct used.

In some embodiments, the eukaryotic cell comprises an expression vector with nucleic acids encoding Smart CAR(s), DE-CAR(s), Smart-DE-CAR(s), and/or Side-CARs of the invention. In some embodiments, the eukaryotic cell of the invention is a mammalian cell. In some embodiments, the eukaryotic cell is a human cell or a murine cell. In some embodiments, the eukaryotic cell is a cell within the hematopoietic lineage. In some embodiments, the eukaryotic cell is a T-lymphocyte, a natural killer cell, a B-lymphocyte, or a macrophage. In some embodiments, the eukaryotic cell of the invention has a desired amount of CAR, DE-CAR, and/or Side-CAR polypeptide(s). In some embodiments, the eukaryotic cell has a desired amount of CAR, DE-CAR, and/or Side-CAR polypeptide(s) on its surface. In some embodiments, the eukaryotic cell with the CAR, DE-CAR, and/or Side-CAR polypeptide(s) of the invention has a desired amount potential of proliferative activity.

In some embodiments, the polynucleotide encoding the Smart CAR, DE-CAR, Smart-DE-CAR, and/or Side-CAR is/are integrated into a chromosome of the eukaryotic cell. In some embodiments, the polynucleotide encoding the Smart CAR, DE-CAR, Smart-DE-CAR, and/or Side-CAR is present in the eukaryotic cell extrachromosomally. In some embodiments, the polynucleotide encoding the Smart CAR, DE-CAR, Smart-DE-CAR, and/or Side-CAR is integrated using a genome editing enzyme (CRISPR, TALEN, Zinc-Finger nuclease), and appropriate nucleic acids (including nucleic acids encoding the Smart CAR, DE-CAR, the Smart-DE-CAR, and/or Side CAR). In an embodiment, the genome editing enzymes and nucleic acids integrate the nucleic acid encoding the Smart CAR, DE-CAR, Smart-DE-CAR, and/or Side-CAR at a genomic safe harbor site, such as, for example, the CCR5, AAVS1, human ROSA26, or PSIP1 loci. In some embodiments, the eukaryotic cell is a human T-lymphocyte and the nucleic acid encoding the Smart CAR, DE-CAR, Smart-DE-CAR, and/or Side-CAR is integrated at the CCR5 or PSIP1 loci.

DETAILED DESCRIPTION OF THE INVENTION

Figure 1:
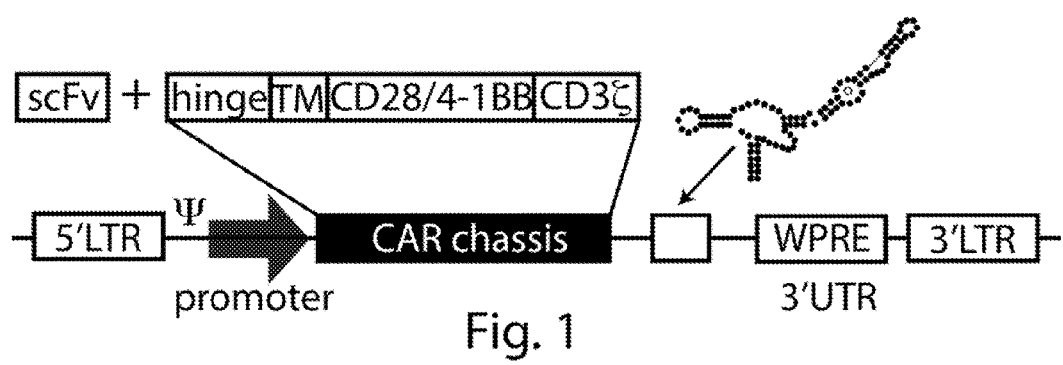
FIG. 1 provides a schematic diagram of a Smart CAR chassis.
Figure 2:
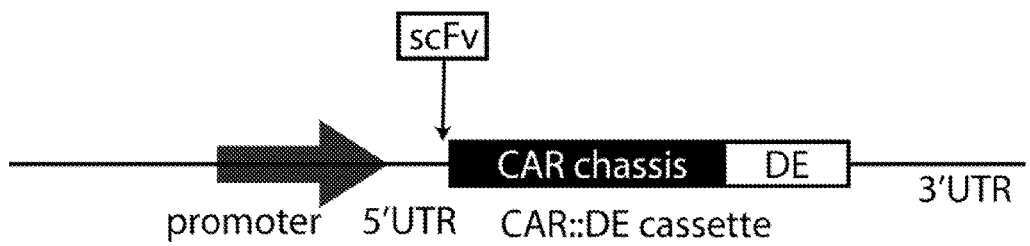
FIG. 2 provides a schematic diagram of a DE-CAR chassis.
Figure 3:
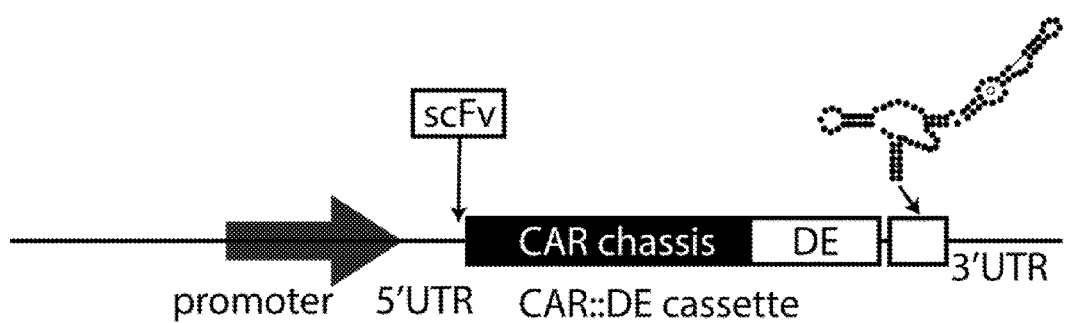
FIG. 3 provides a schematic diagram of a Smart-DE-CAR chassis.

Before the various embodiments are described, it is to be understood that the teachings of this disclosure are not limited to the particular embodiments described, and as such can vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 it is intended that the concentration be understood to be at least approximately or about 10 µg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, an "actuator element" is defined to be a domain that encodes the system control function of the RNA control device. In some embodiments, the actuator domain encodes the gene-regulatory function.

As used herein, an "antibody" is defined to be a protein functionally defined as a ligand-binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as a myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies exist as intact immunoglobulins, as a number of well characterized fragments produced by digestion with various peptidases, or as a variety of fragments made by recombinant DNA technology. Antibodies can derive from many different species (e.g., rabbit, sheep, camel, human, or rodent, such as mouse or rat), or can be synthetic. Antibodies can be chimeric, humanized, or humaneered. Antibodies can be monoclonal or polyclonal, multiple or single chained, fragments or intact immunoglobulins.

As used herein, an "antibody fragment" is defined to be at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either $V_L$ or $V_H$), camelid VHH domains, and multispecific antibodies formed from antibody fragments. The term "scFv" is defined to be a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

As used herein, an "antigen" is defined to be a molecule that provokes an immune response. This immune response may involve either antibody production, or the activation of specific immunologically-competent cells, or both. The skilled artisan will understand that any macromolecule, including, but not limited to, virtually all proteins or peptides, including glycosylated polypeptides, phosphorylated polypeptides, and other post-translation modified polypeptides including polypeptides modified with lipids, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be synthesized or can be derived from a biological sample, or can be a macromolecule besides a polypeptide. Such a biological sample can include, but is not limited to a tissue sample, a tumor sample, a cell or a fluid with other biological components.

As used herein, the term "B-cell" or "B-lymphocyte" are used interchangeably and relate to lymphocytes that produce antibodies. As used herein, B-cells include pro B-cells, pre B-cells, immature B-cells, activated B-cells, plasma cells, memory B-cells and other cells within the B-cell lineage.

As used herein, the terms "Chimeric Antigen Receptor" and the term "CAR" are used interchangeably. As used herein, a "CAR" is defined to be a fusion protein comprising antigen recognition moieties and cell-activation elements.

As used herein, a "CAR T-cell" or "CAR T-lymphocyte" are used interchangeably, and are defined to be a T-cell containing the capability of producing CAR polypeptide, regardless of actual expression level. For example a cell that is capable of expressing a CAR is a T-cell containing nucleic acid sequences for the expression of the CAR in the cell.

As used herein, a "destabilizing element" or a "DE" or a "Degron" are used interchangeably, and are defined to be a polypeptide sequence that is inducibly resistant or susceptible to degradation in the cellular context by the addition or subtraction of a ligand, and which confers this stability modulation to a co-translated polypeptide to which it is fused in cis.

As used herein, an "effective amount" or "therapeutically effective amount" are used interchangeably, and defined to be an amount of a compound, formulation, material, or composition, as described herein effective to achieve a particular biological result.

As used herein, an "epitope" is defined to be the portion of an antigen capable of eliciting an immune response, or the portion of an antigen that binds to an antibody. Epitopes can be a protein sequence or subsequence that is recognized by an antibody.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will be an expression vector or expression construct.

As used herein, the term "fluorescent protein" refers to a protein capable of light emission when excited with an appropriate electromagnetic radiation. Fluorescent proteins include proteins having amino acid sequences that are either natural or engineered.

As used herein, a "hematopoietic cell" is defined to be a cell that arises from a hematopoietic stem cell. This includes but is not limited to myeloid progenitor cells, lymphoid progenitor cells, megakaryocytes, erythrocytes, mast cells, myeloblasts, basophils, neutrophils, eosinophils, macrophages, thrombocytes, monocytes, natural killer cells, T lymphocytes, B lymphocytes and plasma cells.

As used herein, the term "luciferase" refers to a protein that uses a chemical substrate to produce photons. In some embodiments, luciferase refers to an enzyme or photoprotein, such as an oxygenase, that catalyzes a reaction that produces bioluminescence. Luciferases can be recombinant or naturally occurring, or a variant or mutant thereof.

As used herein, the term "reporter" or "reporter molecule" refers to a moiety capable of being detected indirectly or directly. Reporters include, without limitation, a chromophore, a fluorophore, a fluorescent protein, a receptor, a hapten, an enzyme, and a radioisotope.

As used herein, the term "reporter gene" refers to a polynucleotide that encodes a reporter molecule that can be detected, either directly or indirectly. Exemplary reporter genes encode, among others, enzymes, fluorescent proteins, bioluminescent proteins, receptors, antigenic epitopes, and transporters.

As used herein, the term "reporter probe" refers to a molecule that contains a detectable label and is used to detect the presence (e.g., expression) of a reporter molecule. The detectable label on the reporter probe can be any detectable moiety, including, without limitation, an isotope (e.g., detectable by PET, SPECT, etc), chromophore, and fluorophore. The reporter probe can be any detectable molecule or composition that binds to or is acted upon by the reporter to permit detection of the reporter molecule.

As used herein, a "RNA control device" is defined to be an RNA molecule that can adopt different structures and behaviors that correspond to different gene regulatory activities.

As used herein, a "single chain antibody" (scFv) is defined as an immunoglobulin molecule with function in antigen-binding activities. An antibody in scFv (single chain fragment variable) format consists of variable regions of heavy ($V_H$) and light ($V_L$) chains, which are joined together by a flexible peptide linker.

As used herein, a "T-lymphocyte" or T-cell" is defined to be a hematopoietic cell that normally develops in the thymus. T-lymphocytes or T-cells include, but are not limited to, natural killer T cells, regulatory T cells, helper T cells, cytotoxic T cells, memory T cells, gamma delta T cells and mucosal invariant T cells.

As used herein, "transfected" or "transformed" or "transduced" are defined to be a process by which exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

Destabilizing Elements

Destabilizing elements (DE) are stability-affecting polypeptides capable of interacting with a small-molecule ligand, the presence, absence, or amount of which ligand is used to modulate the stability of the DE-polypeptide of interest. In some embodiments, the polypeptide of interest is an immunomodulatory polypeptide. In some embodiments, the polypeptide of interest is a CAR. In some embodiments, binding of ligand by a DE-CAR reduces the degradation rate of the DE-CAR polypeptide in the eukaryotic cell. In some embodiments, binding of ligand by the DE-CAR increases the degradation rate of the DE-CAR in the eukaryotic cell.

Destabilizing elements or DEs useful in the present invention are described in U.S. patent application Ser. No. 15/070,352 filed on Mar. 15, 2016, which is incorporated by reference in its entirety for all purposes. For example, U.S. Ser. No. 15/070,352 describes DEs derived from variants of the FKBP protein, variants of the DHFR protein, variant estrogen receptor binding domain (ERBD), and variant phototropin 1 of *Avena sativa* (AsLOV2). Other examples of variant FKBP nucleic acids and polypeptides are described in US published patent application 20120178168 A1 published on Jul. 12, 2012, which is hereby incorporated by reference in its entirety for all purposes. Other examples of variant DHFR nucleic acids and polypeptides are described in US published patent application 20120178168 A1 published on Jul. 12, 2012, which is hereby incorporated by reference in its entirety for all purposes. Other examples of variant ERBD nucleic acids, polypeptides, and ligands are described in published US patent application 20140255361, which is hereby incorporated by reference in its entirety for all purposes. Other examples of variant AsLOV2 DEs are described in Bonger et al., ACS Chem. Biol. 2014, vol. 9, pp. 111-115, and Usherenko et al., BMC Systems Biology 2014, vol. 8, pp. 128-143, which are incorporated by reference in their entirety for all purposes.

Other DEs can be derived from other ligand binding polypeptides by fusing in frame a nucleic acid encoding the ligand binding polypeptide with a nucleic acid encoding a reporter. This construct is mutagenized by well-known methods, and then mutants with increased or decreased reporter activity in response to ligand binding are identified by a selection or screening. In some embodiments, variants obtained in a first round of mutagenesis and selection/screening are further mutagenized using random mutagenesis and/or creation of combinatorial libraries of the amino acid substitutions obtained in the first round of mutagenesis and/or substitution of other amino acids at the positions identified in the first round of mutagenesis. In some embodiments, the reporter polypeptide is a light emitting polypeptide such as green fluorescent polypeptide (GFP). In some embodiments, the reporter polypeptide can be used in a selection such as, for example, a reporter polypeptide that provides a cell with antibiotic resistance or the ability to grow in a certain nutrient environment or the ability to make a certain essential nutrient (e.g., the enzyme DHFR can be used in selection schemes with certain mammalian cell lines).

Other DEs can be derived from other ligand binding polypeptides using a degron as described above for ERBD. In some embodiments, a degron is fused to the C-terminus of the ligand binding polypeptide. In some embodiments, the degron is fused to the N-terminus of the ligand binding polypeptide. In some embodiments, the ligand binding polypeptide is a ligand binding domain derived from the ligand binding polypeptide, or is some other truncated form of the ligand binding polypeptide that has the ligand binding property. In some embodiments, a nucleic acid encoding the ligand binding domain fused to a degron is fused in frame with a nucleic acid encoding a reporter. This construct is mutagenized by well-known methods, and then mutants with increased or decreased reporter activity in response to ligand binding are identified by a selection or screening. In some embodiments, variants obtained in a first round of mutagenesis and selection/screening are further mutagenized using random mutagenesis and/or creation of combinatorial libraries of the amino acid substitutions obtained in the first round of mutagenesis and/or substitution of other amino acids at the positions identified in the first round of mutagenesis.

Other ligand binding polypeptides from which variants can be made for use as DEs, include for example, enzymes, antibodies or antibody fragments or antibody fragments engineered by recombinant DNA methods with the variable domain, ligand binding receptors, or other proteins. Examples of enzymes include bromodomain-containing proteins, FKBP variants, or prokaryotic DHFR variants. Examples of receptor elements useful in making DEs include: variant ERBD, or other receptors that have ligands which are nontoxic to mammals, especially humans.

In some embodiments, the ligand(s) for the DE are selected for optimization of certain attributes for therapeutic attractiveness. These attributes include specificity to the target DE, affinity to the DE, bioavailability, stability, commercial availability, cost, available related chemical, bio-orthogonality, or combinations thereof. In some embodiments, the ligands are permeable to the plasma membrane, or are transported across the plasma membrane of a eukaryotic cell. In some embodiments, the ligand is orally dosable to a subject. In some embodiments, the ligand is inert (a pro-ligand) and is converted to the active ligand by, for example, chemical means, electromagnetic radiation, or metabolism by normal flora or the subject to produce the active ligand. In some embodiments, the ligand has a serum half-life greater than 1 hour, 2 hours, 4 hours, 6 hours, 8 hours, 12 hours, 24 hours, 48 hours, 96 hours or more. In some embodiments, the ligand has a serum half-life less than 96 hours, 48 hours, 24 hours, 18 hours, 12 hours, 10 hours, 8 hours, 6 hours, 4 hours, 2 hours or 1 hour or less. In some embodiments the ligand has a serum half-life between 1 and 96 hours, between 2 and 48 hours, between 8 and 36 hours, between 10 and 28 hours, between 12 and 24 hours, between 12 and 48 hours, between 8 and 48 hours or between 16 and 18 hours. In some embodiments, the ligand can cross the blood-brain barrier. In some embodiments, the ligand is small and lipophilic. In some embodiments, the ligand cannot normally exist in human bodies or be introduced by normal diet. In some embodiments, the affinity, as measured by Kd, of the ligands to the target DE is less than 1M, 500 mM, 100 mM, 50 mM, 20 mM, 10 mM, 5 mM, 1 mM, 500 µM, 100 µM, 50 µM, 20 µM, 10 µM, 5 µM, 1 µM, 500 nM, 100 nM, 50 nM, 20 nM, 10 nM, 5 nM, 4 nM, 3 nM, 2 nM, 1 nM, 0.5 nM, 0.1 nM or less. In some embodiments, the affinity, as measured by Kd, of the ligands to the target DE is between 1M and 1 pM, between 1 mM and 1 nM, between 100 uM and 1 nM, between 10 uM and 1 nM, between 10 uM and 10 nM, between 10 uM and 100 nM, between 10 uM and 1 uM and between 50 uM and 5 uM, between 1 uM and 500 nM. In some embodiments the ligand is a protein. In some embodiments, the ligand is a small molecule. In some embodiments, the ligand is a nucleic acid.

RNA Control Devices

In some embodiments, the Ribonucleic acid (RNA) control devices of the invention exhibit tunable regulation of gene expression, design modularity, and target specificity. The RNA control devices of the invention can act to rewire information flow through cellular networks and reprogram cellular behavior in response to changes in the cellular environment. In regulating polypeptide expression, the RNA control devices of the invention can serve as synthetic cellular sensors to monitor temporal and spatial fluctuations in the levels of diverse input molecules. RNA control devices represent powerful tools for constructing ligand-controlled gene regulatory systems tailored to modulate the expression of CAR, DE-CAR, Side-CAR and/or other polypeptides of the invention in response to specific effector molecules enabling RNA regulation of target CAR, DE-CAR, Side-CAR and/or other polypeptide constructs in various living systems.

The RNA control devices of the invention may be either trans-acting or cis-acting. By trans-acting, it is meant that the RNA control device exerts its ligand-dependent activity on a molecule, e.g. another nucleic acid, that is different from the RNA control device, e.g. not linked through a phosphodiester (or equivalent) backbone linker, and even more preferably not covalently linked to the RNA control device at all. By cis-acting, it is meant that the RNA control device exerts its ligand-dependent activity on the same contiguous nucleic acid, i.e., a nucleic acid that is covalently linked to the RNA control device, e.g., through a phosphodiester (or equivalent) backbone linker.

In some embodiments, the RNA control devices of the invention comprise a regulatory element and a sensor element. In some embodiments, the RNA control devices of the invention comprise a single element with both a regulatory and sensory function. In some embodiments, the RNA control devices of the invention comprise a regulatory function and a sensory function. In some embodiments, the RNA control devices of the invention comprise a regulatory element, a sensor element, and an information transmission element (ITE) that functionally couples the regulatory element and the sensor element. In some embodiments, the ITE of the subject invention is based on, for example, a strand-displacement mechanism, an electrostatic interaction, a conformation change, or a steric effect. In some embodiments, the sensing function of the RNA control device leads to a structural change in the RNA control device, leading to altered activity of the regulatory function. Some mechanisms whereby these structural changes can occur include steric effects, hydrophobicity driven effects (log p), electrostatically driven effects, nucleotide modification effects (such as methylation, etc.), secondary ligand interaction effects and other effects. In some embodiments, a strand-displacement mechanism uses competitive binding of two nucleic acid sequences (e.g., the competing strand and the RNA control device strand) to a general transmission region of the RNA control device (e.g., the base stem of the aptamer) to result in disruption or restoration of the regulatory element in response to ligand binding to the sensor element.

In some embodiments, the sensor element-regulated nucleic acids are designed such that it can adopt at least two distinct conformations. In one conformation, the sensor element is capable of binding to a ligand, and the regulatory element may be in one activity state (e.g., more active state or less active state). In the other conformation, the sensor element is incapable of binding to the ligand, and regulatory element may be in another activity state. The conformation change of the sensor element may be transmitted through the information transmission element to the coupled regulatory element, so that the regulatory element adopts one of the two activity states depending on whether the sensor element can or cannot bind the ligand.

In some embodiments, the aptamer-regulated nucleic acid platform is fully modular, enabling ligand response and regulatory function (e.g., transcript targeting) to be engineered by swapping elements within the subject regulated nucleic acid. This provides a platform for the construction of tailor-made sensor element regulated nucleic acids for a variety of different ligands. Ligand binding of the sensor element in sensor-regulated nucleic acids is designed separately from the targeting capability of the regulatory element by swapping only the sensor element. Likewise, the targeting capability of the regulatory element can be designed separately from the ligand binding of the sensor element by swapping the regulatory element so that a different gene or molecule is targeted without affecting the sensor element. Thus, the subject sensor element-regulated nucleic acids present a powerful, flexible method of tailoring spatial and temporal gene expression in both natural and engineered contexts.

In some embodiments, the RNA control devices are cis-acting RNA sequences that regulate the production of cognate protein encoded by a messenger RNA (mRNA). In some embodiments RNA control devices comprise RNA with sequences that enable direct or indirect binding of a ligand. In some embodiments, binding of a ligand to the RNA control device increases or decreases the amount of protein translated from the mRNA. In some embodiments, RNA control devices comprise riboswitches which are segments of mRNA that bind a small molecule.

An example of an RNA control device is the theophylline responsive switch, comprising an aptamer (a ligand binding component) and hammerhead ribozyme (gene regulating component) (Win and Smolke 2007 PNAS 104 (36): 14283-88, which is hereby incorporated by reference in its entirety for all purposes). Upon aptamer binding of theophylline, the ribozyme becomes inactive and enables the expression of the desired transgene. In the absence of theophylline the ribozyme self cleaves, leading to nuclease driven degradation of the mRNA, inhibiting translation of the mRNA into protein.

In some embodiments, the RNA control device comprises a sensor element and a regulatory element. In some embodiments the sensor element is an RNA aptamer. In some embodiments, the RNA control device comprises more than one sensor element. In some embodiments the regulatory element is a ribozyme. In some embodiments the ribozyme is a hammerhead ribozyme. In some embodiments, the ribozyme is a hairpin ribozyme, or a hepatitis delta virus (HDV) ribozyme, or a Varkud Satellite (VS) ribozyme, or a glmS ribozyme. In other embodiments the ribozyme is a ribozyme known in the art.

In some embodiments, the RNA control device is embedded within a nucleic acid that encodes a transgene. In some embodiments the transgene of interest encodes a chimeric antigen receptor, a DE-chimeric antigen receptor, or a Side CAR.

In some embodiments an RNA control device or devices are embedded within a DNA sequence. In some embodiments, the RNA control device is encoded for in messenger RNA. In some embodiments multiple RNA control devices are encoded in cis with a transgene-encoding mRNA. In some embodiments, the RNA control device is repeated. In some embodiments the nucleic acid that is used to encode the RNA control device is repeated. By including multiple RNA control devices, sensitivity and dose response may be tailored or optimized. In some embodiments multiple RNA control devices are included, with each RNA control device being specific for a different ligand. This embodiment can mitigate unintentional expression due to endogenously produced ligands that interact with the sensor element.

RNA Control Devices: Sensor Elements

Sensor elements useful in the present invention are described in U.S. patent application Ser. No. 15/070,352 filed on Mar. 15, 2016, which is incorporated by reference in its entirety for all purposes. In some embodiments, an "aptamer" is a nucleic acid molecule, such as RNA or DNA that is capable of binding to a specific molecule with high affinity and specificity (Ellington et al., Nature 346, 818-22 (1990); and Tuerk et al., Science 249, 505-10 (1990), which are hereby incorporated by reference in their entirety for all purposes). For a review of aptamers that recognize small molecules, see Famulok, Science 9:324-9 (1999), which is hereby incorporated by reference in its entirety for all purposes.

In some embodiments, the binding affinity of the aptamer for its ligand is sufficiently strong and the structure formed by the aptamer when bound to its ligand is significant enough so as to switch an RNA control device of the invention between "on" and "off" states. In some embodiments, the association constant for the aptamer and associated ligand is preferably such that the ligand functions to bind to the aptamer and have the desired effect at the concentration of ligand obtained upon administration of the ligand to a subject. For in vivo use, for example, the association constant should be such that binding occurs well below the concentration of ligand that can be achieved in the serum or other tissue, preferably well below the concentration of ligand that can be achieved intracellularly since cellular membranes may not be sufficiently permeable to allow the intracellular ligand concentration to approach the level in the serum or extracellular environment. In some embodiments, the required ligand concentration for in vivo use is also below that which could have undesired effects on the organism.

Ligands for RNA Control Devices

RNA control devices can be controlled via the addition of exogenous or endogenous ligands. In some embodiments, the ligands are selected for optimization of certain attributes for therapeutic attractiveness. These attributes include specificity to the target RNA control device, affinity to the RNA control device, bioavailability, stability, commercial availability, cost, available related chemical, bio-orthogonality, or combinations thereof. In some embodiments, the ligands are permeable to the plasma membrane, or are transported across the plasma membrane of a eukaryotic cell. In some embodiments, the ligand is orally dosable to a subject. In some embodiments, the ligand is inert (a pro-ligand) and is metabolized by normal flora or the subject to produce the active ligand. In some embodiments, the ligand has a serum half-life greater than 1 hour, 2 hours, 4 hours, 6 hours, 8 hours, 12 hours, 24 hours, 48 hours, 96 hours or more. In some embodiments, the ligand has a serum half-life less than 96 hours, 48 hours, 24 hours, 18 hours, 12 hours, 10 hours, 8 hours, 6 hours, 4 hours, 2 hours or 1 hour or less. In some embodiments the ligand has a serum half-life between 1 and 96 hours, between 2 and 48 hours, between 8 and 36 hours, between 10 and 28 hours, between 12 and 24 hours, between 12 and 48 hours, between 8 and 48 hours or between 16 and 18 hours. In some embodiments, the ligand can cross the blood-brain barrier. In some embodiments, the ligand is small and lipophilic. In some embodiments, the ligand cannot normally exist in human bodies or be introduced by normal diet. In some embodiments, the affinity, as measured by Kd, of the ligands to the target RNA control device is less than 1M, 500 mM, 100 mM, 50 mM, 20 mM, 10 mM, 5 mM, 1 mM, 500 µM, 100 µM, 50 µM, 20 µM, 10 µM, 5 µM, 1 µM, 500 nM, 100 nM, 50 nM, 20 nM, 10 nM, 5 nM, 4 nM, 3 nM, 2 nM, 1 nM, 0.5 nM, 0.1 nM or less. In some embodiments, the affinity, as measured by Kd, of the ligands to the target DE is between 1M and 1 pM, between 1 mM and 1 nM, between 100 uM and 1 nM, between 10 uM and 1 nM, between 10 uM and 10 nM, between 10 uM and 100 nM, between 10 uM and 1 uM and between 50 uM and 5 uM, between 1 uM and 500 nM. In some embodiments the ligand is a protein. In some embodiments, the ligand is a small molecule. In some embodiments, the ligand is a nucleic acid.

In some embodiments, the ligand is a naturally occurring, secreted metabolite. For example, a ligand that is uniquely produced by a tumor, or present in the tumor microenvironment is the ligand for the sensor element and binding of this ligand to the sensor element changes the activity of the RNA control device. Thus the control device is responsive and controlled through chemical signaling or proximity to a tumor.

In some embodiments, the ligand is selected for its pharmacodynamic or ADME behavior. For example ligands may be preferentially localized to specific portions of the human anatomy and physiology. For example certain molecules are preferentially absorbed or metabolized in the gut, the liver, the kidney etc. In some embodiments the ligand is selected to demonstrate preferential pharmacodynamic behavior in a particular organ. For example, it would be useful to have a ligand that preferentially localizes to the colon for a colorectal carcinoma so that the peak concentration of the ligand is at the required site, whereas the concentrations in the rest of the body is minimized, preventing undesired, nonspecific toxicity. In some embodiments the ligand is selected to demonstrate non preferential pharmacodynamic behavior. For example, for disseminated tumors like hematological malignancies, it would be useful to have non variant concentration of the ligand throughout the body.

RNA Control Devices: Regulatory Elements

In some embodiments, the regulatory element comprises a ribozyme, or an antisense nucleic acid, or an RNAi sequence or precursor that gives rise to a siRNA or miRNA, or a shRNA or precursor thereof, or an RNAse III substrate, or an alternative splicing element, or a transcription terminator, or a ribosome binding site, or an IRES, or a polyA site. Regulatory elements useful in the present invention are described in U.S. patent application Ser. No. 15/070,352 filed on Mar. 15, 2016, which is incorporated by reference in its entirety for all purposes.

General approaches to constructing oligomers useful in antisense technology have been reviewed, for example, by van der Krol et al. (1988) Biotechniques 6:958-976; and Stein et al. (1988) Cancer Res 48:2659-2668, which are hereby incorporated by reference in their entirety for all purposes. Certain miRNAs that may be used in the invention are described in Brennecke et al., Genome Biology 4:228 (2003); Kim et al., Mol. Cells. 19:1-15 (2005), which are hereby incorporated by reference in their entirety for all purposes.

In some embodiments, the RNA control devices have multiple regulatory elements, and/or multiple sensor elements. In some embodiments, the multiple sensor elements recognize different ligands. In some embodiments, the multiple sensor elements have different effects on the regulatory element.

Chimeric Antigen Receptors

In some embodiments, chimeric antigen receptors (CARs) are fused proteins comprising an extracellular antigen-binding/recognition element, a transmembrane element that anchors the receptor to the cell membrane and at least one intracellular element. These CAR elements are known in the art, for example as described in patent application US20140242701, which is incorporated by reference in its entirety for all purposes herein. In some embodiments, the CAR of the invention is a recombinant polypeptide construct comprising at least an extracellular antigen binding element, a transmembrane element and an intracellular signaling element comprising a functional signaling element derived from a stimulatory molecule. In some embodiments, the stimulatory molecule is the zeta chain associated with the T cell receptor complex. In some embodiments, the cytoplasmic signaling element further comprises one or more functional signaling elements derived from at least one costimulatory molecule. In some embodiments, the costimulatory molecule is chosen from 4-1BB (i.e., CD137), CD27 and/or CD28. In some embodiments, the CAR comprises a chimeric fusion protein comprising an extracellular antigen recognition element, a transmembrane element and an intracellular signaling element comprising a functional signaling element derived from a stimulatory molecule. In some embodiments, the CAR comprises a chimeric fusion protein comprising an extracellular antigen recognition element, a transmembrane element and an intracellular signaling element comprising a functional signaling element derived from a co-stimulatory molecule and a functional signaling element derived from a stimulatory molecule. In some embodiments, the CAR comprises a chimeric fusion protein comprising an extracellular antigen recognition element, a transmembrane element and an intracellular signaling element comprising two functional signaling elements derived from one or more co-stimulatory molecule(s) and a functional signaling element derived from a stimulatory molecule. In some embodiments, the CAR comprises a chimeric fusion protein comprising an extracellular antigen recognition element, a transmembrane element and an intracellular signaling element comprising at least two functional signaling elements derived from one or more co-stimulatory molecule(s) and a functional signaling element derived from a stimulatory molecule. In some embodiments, the CAR comprises an optional leader sequence at the amino-terminus (N-term) of the CAR fusion protein. In some embodiments, the CAR further comprises a leader sequence at the N-terminus of the extracellular antigen recognition element, wherein the leader sequence is optionally cleaved from the antigen recognition element (e.g., a scFv) during cellular processing and localization of the CAR to the cellular membrane.

Chimeric Antigen Receptor—Extracellular Element

Extracellular elements useful in the present invention are described in U.S. patent application Ser. No. 15/070,352 filed on Mar. 15, 2016, which is incorporated by reference in its entirety for all purposes.

In some embodiments, the extracellular element(s) can be obtained from the repertoire of antibodies obtained from the immune cells of a subject that has become immune to a disease, such as for example, an infectious disease, cancer, or other diseases. In some embodiments, a library of extracellular element-CARs is made from the repertoire of antibodies obtained from the immune cells of a subject that has become immune to a disease. In some embodiments, the subject has become immune to an infectious disease. In some embodiments, the extracellular element may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In some embodiments, the extracellular element(s) can be obtained from the repertoire of T-cell receptors obtained from the immune cells of a subject that has become immune to a disease or had an immune reaction to a disease. In some embodiments, a library of extracellular element-CARs is made from the repertoire of T-cell receptors obtained from the immune cells of a subject that has become immune to a disease or had an immune reaction to a disease.

In some embodiments, the antigen binding domain is from a receptor such as, for example the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105). In some embodiments, a library of extracellular element-CARs is made from innate immunity receptors from natural killer cells and/or Toll-like receptors from natural killer cells, dendritic cells, macrophages, T-cells, and B-cells that are obtained from a subject who has become immune to a disease or had an immune reaction to a disease.

As described in U.S. Pat. Nos. 5,359,046, 5,686,281 and 6,103,521 (which are hereby incorporated by reference in their entirety for all purposes), the extracellular element may be obtained from any of the wide variety of extracellular proteins (including receptors, membrane bound ligands, and other proteins associated with the membrane) or secreted proteins associated with ligand binding and/or signal transduction. In some embodiments, the extracellular element is part of a protein which is monomeric, homodimeric, heterodimeric, or associated with a larger number of proteins in a non-covalent complex. In some embodiments, extracellular proteins for use as extracellular elements are molecular complexes of proteins where only one chain has the major role of binding to ligand. In this embodiment, the extracellular element can be derived from the extracellular portion of the ligand binding protein. In some embodiments, the extracellular protein is a complex of extracellular portions from several proteins that may be covalently bonded through disulfide linkages. In this embodiment, the extracellular element of a CAR may also provide for the formation of such multimeric extracellular complexes. In some embodiments, the extracellular element is comprised of truncated portions of the extracellular protein, where such truncated portion is functional for binding ligand.

In some embodiments, there is provided a Smart CAR, DE-CAR, Smart-DE-CAR, and/or Side-CAR capable of binding to an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

In some embodiments, antigens specific for infectious diseases targeted by the Smart CAR(s), DE-CAR(s), Smart-DE-CAR(s), and/or Side-CARs of the invention include but are not limited to any one or more of anthrax toxin, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-α. Other antigens specific for infectious diseases will be apparent to those of skill in the art and may be used in connection with alternate embodiments of the invention.

In some embodiments, there is provided a Smart CAR, DE-CAR, Smart-DE-CAR, and/or Side CAR capable of binding to an antigen associated with a bacterial strain of *Staphylococci, Streptococcus, Escherichia coli, Pseudomonas*, or *Salmonella*. In some embodiments, a phagocytic immune cell is engineered with a Smart CAR, DE-CAR, Smart-DE-CAR, and/or Side CAR specific for these or other pathogenic bacteria. Such Smart CAR, DE-CAR, Smart-DE-CAR, and/or Side CAR engineered immune cells are useful in treating bacterial infections. Examples of bacterial pathogens that can be targeted by such Smart CAR(s), DE-CAR(s), Smart-DE-CAR(s), and/or Side-CARs include, *Staphylococcus aureus, Neisseria gonorrhoeae, Streptococcus pyogenes*, Group A *Streptococcus*, Group B *Streptococcus* (*Streptococcus agalactiae*), *Streptococcus pneumoniae*, and *Clostridium tetani*. In some embodiments, there is provided a Smart CAR, DE-CAR, Smart-DE-CAR, and/or Side CAR capable of binding to an antigen found on host cells infected with an infectious pathogen (e.g., a virus, a bacteria, a protozoan, or a fungus). Examples of bacterial pathogens that may infect host cells include, *Helicobacter pyloris, Legionella pneumophilia*, a bacterial strain of *Mycobacteria* spp. (e.g. *M. tuberculosis, M. avium, M. intracellulare, M. kansaii*, or *M. gordonea*), *Neisseria meningitides, Listeria monocytogenes, R. rickettsia, Salmonella* spp., *Brucella* spp., *Shigella* spp., or certain *E. coli* strains or other bacteria that have acquired genes with invasive factors. Examples of viral pathogens that may infect host cells include, Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

In some embodiments, there is provided a Smart CAR, DE-CAR, Smart-DE-CAR, and/or Side CAR capable of binding to a tumor antigen such as any one or more of 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD21, CD22, CD23 (IgE receptor), CD28, CD30 (TNFRSF8), CD33, CD4, CD40, CD44 v6, CD51, CD52, CD56, CD74, CD80, CEA, CNTO888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, alpha 5β1-integrin, integrin αvβ3, MORAb-009, MS4A1, MUC1, mucin CanAg, N-glycolylneuraminic acid, NPC-1C, PDGF-Rα, PDL192, phosphatidylserine, prostatic carcinoma cells, RANKL, RON, ROR1, SCH 900105, SDC1, SLAMF7, TAG-72, tenascin C, TGF β2, TGF-β, TRAIL-R1, TRAIL-R2, tumor antigen CTAA16.88, VEGF-A, VEGFR-1, VEGFR2, 707-AP, ART-4, B7H4, BAGE, β-catenin/m, Bcr-abl, MN/C IX antibody, CAMEL, CAP-1, CASP-8, CD25, CDC27/m, CDK4/m, CT, Cyp-B, DAM, ErbB3, ELF2M, EMMPRIN, ETV6-AML1, G250, GAGE, GnT-V, Gp100, HAGE, HLA-A*0201-R170I, HPV-E7, HSP70-2M, HST-2, hTERT (or hTRT), iCE, IL-2R, IL-5, KIAA0205, LAGE, LDLR/FUT, MAGE, MART-1/melan-A, MART-2/Ski, MC1R, myosin/m, MUM-1, MUM-2, MUM-3, NA88-A, PAP, proteinase-3, p190 minor bcr-abl, Pml/RARα, PRAME, PSA, PSM, PSMA, RAGE, RU1 or RU2, SAGE, SART-1 or SART-3, survivin, TPI/m, TRP-1, TRP-2, TRP-2/INT2, WT1, NY-Eso-1 or NY-Eso-B or vimentin. Other antigens specific for cancer will be apparent to those of skill in the art and may be used in connection with alternate embodiments of the invention.

In some embodiments, antigens specific for senescent cells are targeted by the CAR, DE-CAR, Smart-DE-CAR, and/or Side-CARs of the invention include but are not limited to any one or more of DEP1, NTAL, EBP50, STX4, VAMP3, ARMX3, B2MG, LANCL1, VPS26A, or PLD3. Other antigens specific for senescent cells will be apparent to those of skill in the art and may be used in connection with alternate embodiments of the invention. See, e.g., Althubiti et al., Cell Death and Disease vol. 5, p. e1528 (2014), which is incorporated by reference in its entirety for all purposes.

Other targets for extracellular elements are described in U.S. patent application Ser. No. 15/070,352 filed on Mar. 15, 2016, which is incorporated by reference in its entirety for all purposes.

Intracellular Element

In some embodiments, the intracellular element is a molecule that can transmit a signal into a cell when the extracellular element of the Smart CAR, DE-CAR, Smart-DE-CAR, and/or Side CAR binds to (interacts with) an antigen. In some embodiments, the intracellular signaling element is generally responsible for activation of at least one of the normal effector functions of the immune cell in which the Smart CAR, DE-CAR, Smart-DE-CAR, and/or Side CAR has been introduced. The term "effector function" refers to a specialized function of a cell. Effector function of a T cell, for example, may be cytolytic activity or helper activity including the secretion of cytokines. Thus the term "intracellular signaling element" refers to the portion of a protein which transduces the effector function signal and directs the cell to perform a specialized function. While the entire intracellular signaling domain can be employed, in many cases the intracellular element or intracellular signaling element need not consist of the entire domain. To the extent that a truncated portion of the intracellular signaling domain is used, such truncated portion may be used as long as it transduces the effector function signal. The term intracellular signaling element is thus also meant to include any truncated portion of the intracellular signaling domain sufficient to transduce the effector function signal. Examples of intracellular signaling elements for use in the Smart CAR, DE-CAR, Smart-DE-CAR, and/or Side CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

Intracellular elements and combinations polypeptides useful with or as intracellular elements are described in U.S. patent application Ser. No. 15/070,352 filed on Mar. 15, 2016, which is incorporated by reference in its entirety for all purposes.

Transmembrane Element and Spacer Element

The Smart CAR, DE-CAR, Smart-DE-CAR, and/or Side CAR of the present invention comprises a transmembrane element. The transmembrane element is attached to the extracellular element of the Smart CAR, DE-CAR, Smart-DE-CAR, and/or Side CAR. In some embodiments, a transmembrane element includes one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In some embodiments, the transmembrane element is associated with one of the other elements used in the Smart CAR, DE-CAR, Smart-DE-CAR, and/or Side CAR. In some embodiments, the transmembrane element is selected or modified by amino acid substitution to avoid binding of such elements to the transmembrane elements of the same or different surface membrane proteins, e.g., to minimize interactions with other members of the receptor complex. In some embodiments, the transmembrane element is capable of homodimerization with another Smart CAR, DE-CAR, Smart-DE-CAR, and/or Side CAR on the cell surface. In some embodiments, the amino acid sequence of the transmembrane element may be modified or substituted so as to minimize interactions with the binding elements of the native binding partner present in the same cell.

The transmembrane element may be contributed by the protein contributing the multispecific extracellular inducer clustering element, the protein contributing the effector function signaling element, the protein contributing the proliferation signaling portion, or by a totally different protein. For the most part it will be convenient to have the transmembrane element naturally associated with one of the elements. In some cases it will be desirable to employ the transmembrane element of the ζ or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. In some embodiments, the transmembrane element will be selected or modified by amino acid substitution to avoid binding of such elements to the transmembrane elements of the same or different surface membrane proteins to minimize interactions with other members of the receptor complex. In some embodiments it will be desirable to employ the transmembrane element of ζ, η, FcεR1-γ and -β, MB1 (Igα), B29 or CD3-γ, ζ, or ε, in order to retain physical association with other members of the receptor complex.

Transmembrane elements useful in the present invention are described in U.S. patent application Ser. No. 15/070,352 filed on Mar. 15, 2016, which is incorporated by reference in its entirety for all purposes.

Chimeric Antigen Receptors Coupled with Destabilizing Elements (DE-CAR)

In some embodiments of the present invention, destabilizing elements, as described above, are combined in cis with a CAR, as described above, so that the amount of the CAR polypeptide in the eukaryotic cell is under the control of the DE. This is one embodiment of the DE-CAR of the invention. DE-CARs, selection of DEs, and use of one or multiple DEs in the present invention are described in U.S. patent application Ser. No. 15/070,352 filed on Mar. 15, 2016, which is incorporated by reference in its entirety for all purposes.

Chimeric Antigen Receptors: Side-CARs

In some embodiments, the CARs, Smart CARs, DE-CAR, and/or Smart-DE-CARs of the invention are comprised of at least two parts which associate to form a functional CAR or DE-CAR. In some embodiments, the extracellular antigen binding element is expressed as a separate part from the transmembrane element, optional spacer, and the intracellular element of a CAR. In some embodiments, the separate extracellular binding element is associated with the host cell membrane (through a means other than a transmembrane polypeptide). In some embodiments, the intracellular element is expressed as a separate part from the extracellular element, transmembrane element, and optionally the spacer. In some embodiments the extracellular element and intracellular element are expressed separately and each has a transmembrane element, and optionally a spacer. In some embodiments, each part of the CAR or DE-CAR has an association element ("Side-CAR") for bringing the two parts together to form a functional CAR or DE-CAR.

Side CARs, selection of Side CARs, and their use with or without a tether are described in U.S. patent application Ser. No. 15/070,352 filed on Mar. 15, 2016, which is incorporated by reference in its entirety for all purposes.

Lymphocyte Expansion Molecule and Other Regulatory Factors

The use of DEs and/or RNA control devices in the invention to control expression of lymphocyte expansion molecule ("LEM"), IL1, IL2, IL4, IL5, IL6, IL7, IL10, IL12, IL15, GM-CSF, G-CSF, TNFα, and/or IFNγ is described in U.S. patent application Ser. No. 15/070,352 filed on Mar. 15, 2016, which is incorporated by reference in its entirety for all purposes.

Eukaryotic Cells

In the present invention, various eukaryotic cells can be used as the eukaryotic cell of the invention. In some embodiments, the eukaryotic cells of the invention are animal cells. In some embodiments, the eukaryotic cells are mammalian cells, such as mouse, rat, rabbit, hamster, porcine, bovine, feline, or canine. In some embodiments, the mammalian cells are cells of primates, including but not limited to, monkeys, chimpanzees, gorillas, and humans. In some embodiments, the mammalians cells are mouse cells, as mice routinely function as a model for other mammals, most particularly for humans (see, e.g., Hanna, J. et al., *Science* 318:1920-23, 2007; Holtzman, D. M. et al., *J Clin Invest.* 103(6):R15-R21, 1999; Warren, R. S. et al., *J Clin Invest.* 95: 1789-1797, 1995; each publication is incorporated by reference in its entirety for all purposes). Animal cells include, for example, fibroblasts, epithelial cells (e.g., renal, mammary, prostate, lung), keratinocytes, hepatocytes, adipocytes, endothelial cells, and hematopoietic cells. In some embodiments, the animal cells are adult cells (e.g., terminally differentiated, dividing or non-dividing) or embryonic cells (e.g., blastocyst cells, etc.) or stem cells. In some embodiments, the eukaryotic cell is a cell line derived from an animal or other source.

In some embodiments, the eukaryotic cell is a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells of the invention. In some embodiments, the eukaryotic cells are derived from any of these circulating eukaryotic cells. The present invention may be used with any of these circulating cells or eukaryotic cells derived from the circulating cells. In some embodiments, the eukaryotic cell is a T-cell or T-cell precursor or progenitor cell. In some embodiments, the eukaryotic cell is a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. In some embodiments, the eukaryotic cell is a natural killer cell, or a precursor or progenitor cell to the natural killer cell. In some embodiments, the eukaryotic cell is a B-cell, or a plasma cell, or a B-cell precursor or progenitor cell. In some embodiments, the eukaryotic cell is a neutrophil or a neutrophil precursor or progenitor cell. In some embodiments, the eukaryotic cell is a megakaryocyte or a precursor or progenitor cell to the megakaryocyte. In some embodiments, the eukaryotic cell is a macrophage or a precursor or progenitor cell to a macrophage.

In some embodiments, a source of cells is obtained from a subject. The subject may be any living organisms. In some embodiments, the cells are derived from cells obtained from a subject. Examples of subjects include humans, dogs, cats, mice, rats, and transgenic species thereof. In some embodiments, T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as Ficoll separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In an alternative aspect, the wash solution lacks calcium and may lack magnesium or may lack many if not all divalent cations. Initial activation steps in the absence of calcium can lead to magnified activation.

In some embodiments, the host T-lymphocytes are modified to reduce apoptosis mediated killing of target cells by CAR, Smart CAR, DE-CAR, Smart-DE-CAR, and/or Side- CAR T-cells. For example, the host T-cells can be genetically modified to knock-out FasL which will prevent the CAR, Smart CAR, DE-CAR, Smart-DE-CAR, and/or Side-CAR T-cell from killing target cells by FasL mediated apoptosis. In some embodiments, FasL is knocked out using the CRISPR/Cas9, TALEN, Zinc-Finger Nuclease, or equivalent systems (e.g., Cong et al. Science 339.6121 (2013): 819-823, Li et al. *Nucl. Acids Res* (2011): gkr188, Gaj et al. Trends in Biotechnology 31.7 (2013): 397405, all of which are incorporated by reference in their entirety for all purposes). In some embodiments, double allele knock-outs of the FasL gene can be obtained using a dual antibiotic resistant selection with Cas9 as described in Park et al., PLoS One 9:e95101 (2014), which is incorporated by reference in its entirety for all purposes, or the Cas9 gRNA approach as described in Zhang et al., Methods 69:171-178 (2014), which is incorporated by reference in its entirety for all purposes. In some embodiments, double allele knock outs are obtained using a Cas9 system with multiple gRNAs targeted to the FasL gene of the host T-cell. These host T-lymphocytes with a double knockout of FasL are then used as host cells for the CAR, Smart CAR, DE-CAR, Smart-DE-CAR, and/or Side-CAR constructs of the invention.

Enrichment of a T cell population by negative selection can be accomplished with a combination of antibodies directed to surface markers unique to the negatively selected cells. In some embodiments, cells are enriched by cell sorting and/or selection via negative magnetic immunoadherence or flow cytometry using a cocktail of monoclonal antibodies directed to cell surface markers present on the cells. For example, to enrich for CD4+ cells, a monoclonal antibody cocktail typically includes antibodies to CD14, CD20, CD11b, CD16, HLA-DR, and CD8. In some embodiments, it may be desirable to enrich for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

T cells may be activated and expanded generally using methods as described, for example, in U.S. Pat. Nos. 6,352, 694; 6,534,055; 6,905,680; 6,692,964; 5,858,358; 6,887, 466; 6,905,681; 7,144,575; 7,067,318; 7,172,869; 7,232, 566; 7,175,843; 5,883,223; 6,905,874; 6,797,514; 6,867, 041; and U.S. Patent Application Publication No. 20060121005, each of which is incorporated by reference in its entirety for all purposes.

In some embodiments, NK cells may be expanded in the presence of a myeloid cell line that has been genetically modified to express membrane bound IL-15 and 4-1BB ligand (CD137L). A cell line modified in this way which does not have MEW class I and II molecules is highly susceptible to NK cell lysis and activates NK cells. For example, K562 myeloid cells can be transduced with a chimeric protein construct consisting of human IL-15 mature peptide fused to the signal peptide and transmembrane domain of human CD8a and GFP. Transduced cells can then be single-cell cloned by limiting dilution and a clone with the highest GFP expression and surface IL-15 selected. This clone can then be transduced with human CD137L, creating a K562-mb15-137L cell line. To preferentially expand NK cells, peripheral blood mononuclear cell cultures containing NK cells are cultured with a K562-mb15-137L cell line in the presence of 10 IU/mL of IL-2 for a period of time sufficient to activate and enrich for a population of NK cells. This period can range from 2 to 20 days, preferably about 5 days. Expanded NK cells may then be transduced with the anti-CD19-BB-ζ chimeric receptor.

Other host cells useful in the present invention are described in U.S. patent application Ser. No. 15/070,352 filed on Mar. 15, 2016, which is incorporated by reference in its entirety for all purposes.

Nucleic Acids

In some embodiments, the present invention relates to the nucleic acids that encode, at least in part, the individual peptides, polypeptides, proteins, and RNA control devices of the present invention. In some embodiments, the nucleic acids may be natural, synthetic or a combination thereof. The nucleic acids of the invention may be RNA, mRNA, DNA or cDNA.

In some embodiments, the nucleic acids of the invention also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In some embodiments, an exemplary selection scheme utilizes a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

An example of a promoter that is capable of expressing a Smart CAR, DE-CAR, Smart-DE-CAR, and/or Side CAR transgene in a mammalian T cell is the EF1α promoter. The native EF1α promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention is not limited to the use of constitutive promoters.

Inducible promoters are also contemplated as part of the invention. Examples of inducible promoters include, but are not limited to a metallothionein promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822,754, 8,748,125, 8,536,354, all of which are incorporated by reference in their entirety for all purposes.

Expression vectors of the invention typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

In some embodiments, it may be desirable to modify the polypeptides of the present invention. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, *Gene* 8:81-97, 1979; Roberts et al., *Nature* 328:731-734, 1987, which is incorporated by reference in its entirety for all purposes). In some embodiments, the recombinant nucleic acids encoding the polypeptides of the invention are modified to provide preferred codons which enhance translation of the nucleic acid in a selected organism.

The polynucleotides of the invention also include polynucleotides including nucleotide sequences that are substantially equivalent to the polynucleotides of the invention. Polynucleotides according to the invention can have at least about 80%, more typically at least about 90%, and even more typically at least about 95%, sequence identity to a polynucleotide of the invention. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants in accordance with this invention (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y. (1994), each of which is incorporated by reference in its entirety for all purposes. Chemical synthesis using methods well known in the art, such as that described by Engels et al., *Angew Chem Intl Ed.* 28:716-34, 1989 (which is incorporated by reference in its entirety for all purposes), may also be used to prepare such nucleic acids.

In some embodiments, amino acid "substitutions" for creating variants are preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

The present invention provides a nucleic acid encoding the Smart CAR, DE-CAR, Smart-DE-CAR, and/or Side CAR of the invention. The nucleic acid encoding the Smart CAR, DE-CAR, Smart-DE-CAR, and/or Side CAR can be easily prepared from an amino acid sequence of the specified CAR combined with the sequence of the RNA control device by a conventional method. A base sequence encoding an amino acid sequence can be obtained from the aforementioned NCBI Ref or accession numbers of GenBenk for an amino acid sequence of each element, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid of the present invention can be linked to another nucleic acid so as to be expressed under control of a suitable promoter. The nucleic acid of the present invention can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

When the nucleic acid of the present invention is introduced into a cell ex vivo, the nucleic acid of the present invention may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful. Particularly, a composition in a form suitable for administration to a living body which contains the nucleic acid of the present invention carried by a suitable vector is suitable for in vivo gene therapy.

Reporters

In some embodiments, a reporter is a moiety capable of being detected indirectly or directly. In some embodiments, the signal from a reporter can be used to quantify an aspect of the system containing the reporter. In some embodiments, reporters include, for example, a chromophore, a fluorophore, a bioluminescent protein, a fluorescent protein, a receptor, a hapten, an enzyme, and a radioisotope. In some embodiments, a reporter is encoded by a reporter gene which polynucleotide encodes a reporter molecule that can be detected, either directly or indirectly. In some embodiments, a reporter probe detects the presence (e.g., expression) of a reporter molecule. The detectable label on the reporter probe can be any detectable moiety, including, without limitation, an isotope, chromophore, and fluorophore. A reporter probe can be any detectable molecule or composition that binds to or is acted upon by the reporter to permit detection of the reporter molecule. In some embodiments, the reporter is a fluorescent reporter, a bioluminescent reporter, other optical reporter, a radioactive reporter, a Positron Emission Tomography (PET) reporter, a Single Photon Emission Computed Tomography (SPECT) reporter, an X-Ray reporter, a photoacoustic reporter, and an ultrasound reporter.

In some embodiments, reporter genes encode, for example, enzymes, fluorescent proteins, bioluminescent proteins, receptors, antigenic epitopes, or transporters. In some embodiments, the enzymes include, for example, β-galactosidase, alkaline phosphatase, chloramphenicol acetyltransferase, horseradish peroxidase, or β-lactamase. In some embodiments, substrates for β-galactosidase include, for example, ONPG (o-nitrophenyl-β-D-galactopyranoside), Galacton-Plus®, Galacton-Star®, which are commercially available from ThermoFisher Scientific. In some embodiments, substrates for alkaline phosphatase include, for example, PNPP (p-Nitrophenyl Phosphate, Disodium Salt), CSPD® chemiluminescent substrate, 1,2-di oxetane chemiluminescent substrate, DynaLight™ Substrate with RapidGlow™ Enhancer, which are all commercially available from ThermoFisher Scientific. In some embodiments, substrates for chloramphenicol acetyltransferase include, for example, FAST CAT® Green (deoxy), which is commercially available from ThermoFisher Scientific. In some embodiments, substrates for horseradish peroxidase include, for example, ABTS (2,2'-Azinobis [3-ethylbenzothiazoline-6-sulfonic acid]-diammonium salt), OPD (o-phenylenediamine dihydrochloride), TMB (3,3',5,5'-tetramethylbenzidine), SuperSignal ELISA Pico Chemiluminescent Substrate, QuantaBlu NS/K Fluorogenic Substrate, QuantaRed Enhanced Chemifluorescent HRP Substrate (ADHP), Amplex Red reagent, all of which are commercially available from ThermoFisher Scientific. In some embodiments, substrates for β-lactamase include, for example, CCF2-FA, CCF2-AM, CCF4-AM, Fluorocillin™ Green reagent, LyticBLAzer™_h-BODIPY® FL Substrate, which is commercially available from ThermoFisher Scientific. Many other enzymes and substrates are well-known in the art and can be used as reporter systems for the invention.

In some embodiments, the fluorescent reporter includes, for example, green fluorescent protein, cyan fluorescent protein, yellow fluorescent protein, orange fluorescent protein, red fluorescent protein, and far-red fluorescent protein, all of which are commercially available from Clontech. In some embodiments, the bioluminescent reporter include, for example, North American firefly luciferase, Japanese firefly luciferase, Italian firefly luciferase, East European firefly luciferase, Pennsylvania firefly luciferase, Click beetle luciferase, railroad worm luciferase, *Renilla* luciferase, *Gaussia* luciferase, *Cypridina* luciferase, *Metrida* luciferase, OLuc, and red firefly luciferase, all of which are commercially available from ThermoFisher Scientific and/or Promega.

In some embodiments, a reporter includes another agent that has a detectable moiety. In some embodiments, the reporter includes an antibody that is labeled with a detectable moiety. In some embodiments, the detectable moiety on the antibody can be an enzyme, a dye (e.g., fluorescein (FITC), phycoerythrin (PE), Cy5PE, Cy7PE, Texas Red (TR), allophycocyanin (APC), Cy5, Cy7APC, cascade blue, Alexa Fluor®, CyDye®, IRDye®, DyLight, ATTO-TEC fluorescent labels, cyanine dyes, rhodamine dyes, fluorescent TrueBlot), a radioisotope, biotin, or haptens. These and other detectable moieties are well known in the art and many are commercially available. In some embodiments, the reporter is a ligand-receptor pair, and is detected by using one member of the pair labeled with a detectable moiety.

In some embodiments, the reporter is detected by optical imaging, ultrasound imaging, computed tomography imaging, magnetic resonance imaging, optical coherence tomography imaging, radiography imaging, nuclear medical imaging, positron emission tomography imaging, tomography imaging, photo acoustic tomography imaging, x-ray imaging, thermal imaging, fluoroscopy imaging, bioluminescent imaging, and fluorescent imaging, magnetic particle imaging, and magnetic resonance spectroscopy.

Process for Producing Eukaryotic Cells Expressing Smart CAR, DE-CAR, Smart-DE-CAR, and/or Side CAR A process for producing a cell expressing the Smart CAR, DE-CAR, Smart-DE-CAR, and/or Side CAR of the present invention includes a step of introducing the nucleic acid encoding a Smart CAR, DE-CAR, Smart-DE-CAR, and/or Side CAR described above into a eukaryotic cell. In some embodiments, this step is carried out ex vivo. For example, a cell can be transformed ex vivo with a virus vector or a non-virus vector carrying the nucleic acid of the present invention to produce a cell expressing the Smart CAR, DE-CAR, Smart-DE-CAR, and/or Side CAR of the present invention.

In the process of the present invention, a eukaryotic cell as describe above is used. In some embodiments, a eukaryotic cell derived from a mammal, for example, a human cell, or a cell derived from a non-human mammal such as a monkey, a mouse, a rat, a pig, a horse, or a dog can be used. The cell used in the process of the present invention is not particularly limited, and any cell can be used. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell, a dendritic cell, a B cell, a hematopoietic stem cell, a macrophage, a monocyte, a NK cell or a hematopoietic cell, an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present invention, particularly, use of a T cell, a precursor cell of a T cell (a hematopoietic stem cell, a lymphocyte precursor cell etc.) or a cell population containing them is preferable. Examples of the T cell include a CD8-positive T cell, a CD4-positive T cell, a regulatory T cell, a cytotoxic T cell, and a tumor infiltrating lymphocyte. The cell population containing a T cell and a precursor cell of a T cell includes a PBMC. The aforementioned cells may be collected from a living body, obtained by expansion culture of a cell collected from a living body, or established as a cell strain. When transplantation of the produced Smart CAR, DE-CAR, Smart-DE-CAR, and/or Side CAR expressing cell or a cell differentiated from the produced Smart CAR, DE-CAR, Smart-DE-CAR, and/or Side CAR expressing cell into a living body is desired, it is preferable to introduce the nucleic acid into a cell collected from the living body itself.

In some embodiments, the nucleic acid encoding the Smart CAR, DE-CAR, Smart-DE-CAR, and/or Side CAR of the present invention is inserted into a vector, and the vector is introduced into a cell. In some embodiments, the nucleic acid encoding the Smart CAR, DE-CAR, Smart-DE-CAR, and/or Side CAR is introduced to the eukaryotic cell by transfection (e.g., Gorman, et al. Proc. Natl. Acad. Sci. 79.22 (1982): 6777-6781, which is incorporated by reference in its entirety for all purposes), transduction (e.g., Cepko and Pear (2001) Current Protocols in Molecular Biology unit 9.9; DOI: 10.1002/0471142727.mb0909s36, which is incorporated by reference in its entirety for all purposes), calcium phosphate transformation (e.g., Kingston, Chen and Okayama (2001) Current Protocols in Molecular Biology Appendix 1C; DOI: 10.1002/0471142301.nsa01cs01, which is incorporated by reference in its entirety for all purposes), cell-penetrating peptides (e.g., Copolovici, Langel, Eriste, and Langel (2014) ACS Nano 2014 8 (3), 1972-1994; DOI: 10.1021/nn4057269, which is incorporated by reference in its entirety for all purposes), electroporation (e.g. Potter (2001) Current Protocols in Molecular Biology unit 10.15; DOI: 10.1002/0471142735.im1015s03 and Kim et al (2014) Genome 1012-19. doi:10.1101/gr.171322.113, Kim et al. 2014 describe the Amaza Nucleofector, an optimized electroporation system, both of these references are incorporated by reference in their entirety for all purposes), microinjection (e.g., McNeil (2001) Current Protocols in Cell Biology unit 20.1; DOI: 10.1002/0471143030.cb2001s18, which is incorporated by reference in its entirety for all purposes), liposome or cell fusion (e.g., Hawley-Nelson and Ciccarone (2001) Current Protocols in Neuroscience Appendix 1F; DOI: 10.1002/0471142301.nsa01fs10, which is incorporated by reference in its entirety for all purposes), mechanical manipulation (e.g. Sharon et al. (2013) PNAS 2013 110(6); DOI: 10.1073/pnas.1218705110, which is incorporated by reference in its entirety for all purposes) or other well-known technique for delivery of nucleic acids to eukaryotic cells. Once introduced, Smart CAR, DE-CAR, Smart-DE-CAR, and/or Side CAR nucleic acid can be transiently expressed episomally, or can be integrated into the genome of the eukaryotic cell using well known techniques such as recombination (e.g., Lisby and Rothstein (2015) Cold Spring Harb Perspect Biol. March 2; 7(3). pii: a016535. doi: 10.1101/cshperspect.a016535, which is incorporated by reference in its entirety for all purposes), or non-homologous integration (e.g., Deyle and Russell (2009) Curr Opin Mol Ther. 2009 August; 11(4):442-7, which is incorporated by reference in its entirety for all purposes). The efficiency of homologous and non-homologous recombination can be facilitated by genome editing technologies that introduce targeted double-stranded breaks (DSB). Examples of DSB-generating technologies are CRISPR/Cas9, TALEN, Zinc-Finger Nuclease, or equivalent systems (e.g., Cong et al. Science 339.6121 (2013): 819-823, Li et al. *Nucl. Acids Res* (2011): gkr188, Gaj et al. Trends in Biotechnology 31.7 (2013): 397-405, all of which are incorporated by reference in their entirety for all purposes), transposons such as Sleeping Beauty (e.g., Singh et al (2014) Immunol Rev. 2014 January; 257(1):181-90. doi: 10.1111/imr.12137, which is incorporated by reference in its entirety for all purposes), targeted recombination using, for example, FLP recombinase (e.g., O'Gorman, Fox and Wahl Science (1991) 15:251(4999):1351-1355, which is incorporated by reference in its entirety for all purposes), CRE-LOX (e.g., Sauer and Henderson *PNAS* (1988): 85; 5166-5170), or equivalent systems, or other techniques known in the art for integrating the nucleic acid encoding the Smart CAR, DE-CAR, Smart-DE-CAR, and/or Side CAR into the eukaryotic cell genome.

In an embodiment, the nucleic acid encoding the Smart CAR, DE-CAR, Smart-DE-CAR, and/or Side CAR is integrated into the eukaryotic cell chromosome at a genomic safe harbor site, such as, for example, the CCR5, AAVS1, human ROSA26, or PSIP1 loci. (Sadelain et al., Nature Rev. 12:51-58 (2012); Fadel et al., J. Virol. 88(17):9704-9717 (2014); Ye et al., PNAS 111(26):9591-9596 (2014), all of which are incorporated by reference in their entirety for all purposes.) In an embodiment, the integration of the nucleic acid encoding the Smart CAR, DE-CAR, Smart-DE-CAR, and/or Side CAR at the CCR5 or PSIP1 locus is done using a gene editing system, such as, for example, CRISPR, TALEN, or Zinc-Finger nuclease systems. In an embodiment, the eukaryotic cell is a human, T-lymphocyte and a CRISPR system is used to integrate the Smart CAR, DE-CAR, Smart-DE-CAR, and/or Side CAR at the CCR5 or PSIP1 locus. In an embodiment, integration of the nucleic acid at CCR5 or PSIP1 using the CRISPR system also deletes a portion, or all, of the CCR5 gene or PSIP1 gene. In an embodiment, Cas9 in the eukaryotic cell may be derived from a plasmid encoding Cas9, an exogenous mRNA encoding Cas9, or recombinant Cas9 polypeptide alone or in a ribonucleoprotein complex. (Kim et al (2014) Genome 1012-19. doi:10.1101/gr.171322.113; Wang et al (2013) Cell 153 (4). Elsevier Inc.: 910-18. doi:10.1016/j.cell.2013.04.025, both of which are incorporated by reference in their entirety for all purposes.)

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In some embodiments, transduction can be done with a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. As the virus vector, a virus vector lacking the replicating ability so as not to self-replicate in an infected cell is preferably used.

In some embodiments, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+en-vAm-12 (U.S. Pat. No. 5,278,056, which is incorporated by reference in its entirety for all purposes), and Psi-Crip (Proceedings of the National Academy of Sciences of the United States of America, vol. 85, pp. 6460-6464 (1988), which is incorporated by reference in its entirety for all purposes). A retrovirus particle can also be prepared using a 293 cell or a T cell having high transfection efficiency. Many kinds of retrovirus vectors produced based on retroviruses and packaging cells that can be used for packaging of the retrovirus vectors are widely commercially available from many companies.

A number of viral based systems have been developed for gene transfer into mammalian cells. A selected gene can be inserted into a vector and packaged in viral particles using techniques known in the art. The recombinant virus can then be isolated and delivered to cells of the subject either in vivo or ex vivo. A number of viral systems are known in the art. In some embodiments, adenovirus vectors are used. A number of adenovirus vectors are known in the art. In some embodiments, lentivirus vectors are used.

In some embodiments, a viral vector derived from a RNA virus is used to introduce the Smart CAR, Smart-DE-CAR, and/or Side-CAR encoding polynucleotides. In some embodiments, the RNA virus vector encodes the reverse complement or antisense strand of the polynucleotide encoding the RNA control device and CAR construct (the complementary strand encodes the sense strand for the RNA control device, DE, CAR and/or Side-CAR construct). In this embodiment, the RNA control device is not active in the single stranded, RNA virus vector. In some embodiments, the sense strand of the RNA control device, DE, CAR and/or Side-CAR construct is encoded in the RNA virus vector, and the viral vector with the RNA control device, DE, CAR and/or Side-CAR construct is maintained and replicated in the presence of ligand for the sensor element of the RNA control device. In some embodiments, the viral vector encoding the sense strand of the RNA control device, DE, CAR and/or Side-CAR construct in the viral vector is maintained and replicated without ligand for the sensor element.

In some embodiments, a non-virus vector is used in combination with a liposome and a condensing agent such as a cationic lipid as described in WO 96/10038, WO 97/18185, WO 97/25329, WO 97/30170 and WO 97/31934 (which are incorporated herein by reference in their entirety for all purposes). The nucleic acid of the present invention can be introduced into a cell by calcium phosphate transduction, DEAE-dextran, electroporation, or particle bombardment.

In some embodiments, chemical structures with the ability to promote stability and/or translation efficiency are used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA. The 5' and 3' UTRs can be the naturally occurring, endogenous 5' and 3' UTRs for the nucleic acid of interest. In some embodiments, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3'UTR sequences can decrease the stability of mRNA. Therefore, 3' UTRs can be selected or designed to increase the stability of the transcribed RNA based on properties of UTRs that are well known in the art.

In some embodiments, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

In the step of introducing a nucleic acid into a cell, a functional substance for improving the introduction efficiency can also be used (e.g. WO 95/26200 and WO 00/01836, which are incorporated herein by reference in their entirety for all purposes). Examples of the substance for improving the introduction efficiency include a substance having ability to bind to a virus vector, for example, fibronectin and a fibronectin fragment. In some embodiments, a fibronectin fragment having a heparin binding site, for example, a fragment commercially available as RetroNectin (registered trademark, CH-296, manufactured by TAKARA BIO INC.) can be used. Also, polybrene which is a synthetic polycation having an effect of improving the efficiency of infection of a retrovirus into a cell, a fibroblast growth factor, V type collagen, polylysine or DEAE-dextran can be used.

In a preferable aspect of the present invention, the functional substance can be used in a state of being immobilized on a suitable solid phase, for example, a container used for cell culture (plate, petri dish, flask or bag) or a carrier (microbeads etc.).

Eukaryotic Cells Expressing the Smart CAR, DE-CAR, Smart-DE-CAR, and/or Side CAR The cell expressing the Smart CAR, DE-CAR, Smart-DE-CAR, and/or Side CAR of the present invention is a cell in which a nucleic acid encoding a Smart CAR, DE-CAR, Smart-DE-CAR, and/or Side CAR is introduced and expressed.

In some embodiments, a eukaryotic cell of the present invention binds to a specific antigen via the CAR, DE-CAR, and/or Side-CAR polypeptide causing the CAR, DE-CAR, and/or Side-CAR polypeptide to transmit a signal into the eukaryotic cell, and as a result, the eukaryotic cell is activated. The activation of the eukaryotic cell expressing the Smart CAR, DE-CAR, Smart-DE-CAR, and/or Side CAR is varied depending on the kind of a eukaryotic cell and the intracellular element of the Smart CAR, DE-CAR, Smart-DE-CAR, and/or Side CAR, and can be confirmed based on, for example, release of a cytokine, improvement of a cell proliferation rate, change in a cell surface molecule, or the like as an index.

In some embodiments, eukaryotic cells expressing CAR, Smart CAR, DE-CAR, Smart-DE-CAR, and/or Side CAR constructs are detected using Protein L (a bacterial surface protein isolated from *Peptostreptoccocus magnus* that selectively binds to variable light chains (kappa chain) of immunoglobulins. In some embodiments, Protein L is directly labeled with a reporter (e.g., a light emitting or absorbing moiety) or is labeled with an agent such as biotin. When biotin or related molecule is used to label the Protein L, binding of Protein L to eukaryotic cells displaying CAR, DE-CAR, and/or Side-CAR polypeptide is detected by adding a streptavidin (or similar paired molecule) labeled with reporter (e.g., phycoerythrin). Zheng et al., J. Translational Med., 10:29 (2012), which is incorporated by reference in its entirety for all purposes. Protein L binding to eukaryotic cells containing CAR, Smart CAR, DE-CAR, Smart-DE-CAR, and/or Side CAR constructs demonstrates the presence of antibody light chain, the extracellular domain of a CAR, on the eukaryotic cell. This method of detecting CAR expression on the eukaryotic cell can also be used to quantitate the amount of CAR, DE-CAR, and/or Side-CAR polypeptide on the surface of the eukaryotic cell. In some embodiments, Protein L is used in QC and QA methodologies for making eukaryotic cells with the CAR, Smart CAR, DE-CAR, Smart-DE-CAR, and/or Side CAR constructs of the invention.

In some embodiments, a eukaryotic cell expressing the Smart CAR, DE-CAR, Smart-DE-CAR, and/or Side CAR is used as a therapeutic agent to treat a disease. The therapeutic agent comprises the eukaryotic cell expressing the Smart CAR, DE-CAR, Smart-DE-CAR, and/or Side CAR as an active ingredient, and may further comprise a suitable excipient. Examples of the excipient include pharmaceutically acceptable excipients for the composition. The disease against which the eukaryotic cell expressing the Smart CAR, DE-CAR, Smart-DE-CAR, and/or Side CAR is administered is not particularly limited as long as the disease shows sensitivity to the eukaryotic cell. Examples of diseases of the invention include a cancer (blood cancer (leukemia), solid tumor etc.), hepatitis, or other infectious disease the cause of which is a virus such as influenza and HIV, a bacterium, or a fungus, for example, tuberculosis, MRSA, VRE, and deep mycosis. Other diseases that may be treated with eukaryotic cells expressing the Smart CAR, DE-CAR, Smart-DE-CAR, and/or Side CAR are disclosed in U.S. patent application Ser. No. 15/070,352 filed on Mar. 15, 2016, which is incorporated by reference in its entirety for all purposes.

The eukaryotic cell expressing the Smart CAR, DE-CAR, Smart-DE-CAR, and/or Side CAR of the present invention is administered for treatment of these diseases. The eukaryotic cell of the present invention can also be utilized for prevention of an infectious disease after bone marrow transplantation or exposure to radiation, donor lymphocyte transfusion for the purpose of remission of recurrent leukemia, and the like. The therapeutic agent comprising the eukaryotic cell expressing the Smart CAR, DE-CAR, Smart-DE-CAR, and/or Side CAR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

In some embodiments, the eukaryotic cells with Smart CAR, DE-CAR, Smart-DE-CAR, and/or Side CAR are characterized prior to administration to the subject. In some embodiments, the eukaryotic cells with Smart CAR, DE-CAR, Smart-DE-CAR, and/or Side CAR are tested to confirm Smart CAR, DE-CAR, Smart-DE-CAR, and/or Side CAR expression. In some embodiments, the eukaryotic cells with Smart CAR, DE-CAR, Smart-DE-CAR, and/or Side CAR are exposed to a level of ligand(s) that results in a desired level of CAR, DE-CAR, and/or Side-CAR polypeptide expression in the eukaryotic cell. In some embodiments, this desired level of CAR, DE-CAR, and/or Side-CAR polypeptide produces eukaryotic cells with a desired level of anti-target cell activity, and/or a desired level of proliferative activity when placed in a subject.

In some embodiments, the Smart CAR, DE-CAR, Smart-DE-CAR, and/or Side CAR is used with a T-lymphocyte that has aggressive anti-tumor properties, such as those described in Pegram et al, CD28z CARs and armored CARs, 2014, Cancer J. 20(2):127-133, which is incorporated by reference in its entirety for all purposes. In some embodiments, the RNA control device of the invention is used with an armored CAR, DE-CAR, and/or Side-CAR polypeptide in a T-lymphocyte.

Pharmaceutical Compositions

Pharmaceutical compositions of the present invention may comprise a Smart CAR, DE-CAR, Smart-DE-CAR, and/or Side CAR expressing cell, e.g., a plurality of Smart CAR, DE-CAR, Smart-DE-CAR, and/or Side CAR expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. In some embodiments, an adjuvant such as a wetting agent or an emulsifier, and a pH buffering agent can also be used. In some embodiments, the pharmaceutically acceptable excipients described in Remington's Pharmaceutical Sciences (Mack Pub. Co., N.J. 1991) (which is incorporated herein by reference in its entirety for all purposes) can be appropriately used. The composition of the present invention can be formulated into a known form suitable for parenteral administration, for example, injection or infusion. In some embodiments, the composition of the present invention may comprise formulation additives such as a suspending agent, a preservative, a stabilizer and/or a dispersant, and a preservation agent for extending a validity term during storage.

A composition comprising the eukaryotic cells of the present invention as an active ingredient can be administered for treatment of, for example, a cancer (blood cancer (leukemia), solid tumor etc.), an inflammatory disease/autoimmune disease (asthma, eczema), hepatitis, and an infectious disease the cause of which is a virus such as influenza and HIV, a bacterium, or a fungus, for example, a disease such as tuberculosis, MRSA, VRE, or deep mycosis, depending on an antigen to which a CAR, DE-CAR, and/or Side-CAR polypeptide binds.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, intranasally, intraarterially, intratumorally, into an afferent lymph vessel, by intravenous (i.v.) injection, or intraperitoneally. In one aspect, the T cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection. In some embodiments, the administration is adoptive transfer.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). In some embodiments, a pharmaceutical composition comprising the eukaryotic cells described herein may be administered at a dosage of $10^4$ to $10^9$ cells/kg body weight, in some instances $10^5$ to $10^6$ cells/kg body weight, including all integer values within those ranges. In some embodiments, a eukaryotic cell composition may also be administered multiple times at these dosages. In some embodiments, eukaryotic cells can be administered by using infusion techniques that are commonly known in immunotherapy (see, e.g., Rosenberg et al., New Eng. J. of Med. 319:1676, 1988, which is incorporated by reference in its entirety for all purposes).

Identification of Antigen Binding Domains and CAR Constructs for Treatment of Certain Diseases and Conditions In some embodiments, antigen binding domains and CAR constructs with those antigen binding domains are made from lymphocytes obtained from a subject that has generated an immune response against a disease or condition. In some embodiments, antigen binding domains and CAR constructs with those antigen binding domains are made from lymphocytes obtained from a subject that has generated an effective immune response against a disease or condition. In some embodiments, the antigen binding domains obtained from the subject with immunity are antigen binding domains capable of neutralizing the causative agent of the disease or condition. In some embodiments, the disease is an infectious disease caused by a pathogen. In some embodiments, the pathogen is a virus, a bacterium, or a fungus. In some embodiments, the disease is a cancer. In some embodiments, the condition is an autoimmune disorder. In some embodiments, lymphocytes from the subject are obtained. In some embodiments, the lymphocytes include, for example, B-cells, memory B-cells, plasma cells, and/or pre-B-cells. In some embodiments, lymphocytes include, for example, T-cells, Th1 T-cells, Th2 T-cells, Th17 T-cells, other helper T-cells, Treg T-cells, cytotoxic T-cells, and/or memory T-cells. In some embodiments, lymphocytes are obtained from the peripheral blood of a subject. In some embodiments, the lymphocytes are obtained from the spleen and/or lymph nodes of a subject. In some embodiments, the lymphocytes are obtained from the bone marrow of a subject. In some embodiments, the lymphocytes are obtained from one of more of the peripheral blood, spleen, lymph nodes, and/or bone marrow of a subject. In some embodiments, the lymphocytes are obtained from a mammal. In some embodiments, the lymphocytes are obtained from a mouse. In some embodiments, the lymphocytes are obtained from a rabbit. In some embodiments, the lymphocytes are obtained from a human.

In some embodiments, B-cells and/or B-cell subpopulations (memory B-cells, plasma cells) are isolated from the lymphocytes using techniques known to a person or ordinary skill in the art including, for example, commercially available kits from STEMCELL Technologies, Inc., Miltenyi Biotec, Inc., and Thermo Fisher Scientific, Inc. In some embodiments, T-cells and T-cell subpopulations (memory T-cells, CD8+ T-cells, CD4+ T-cells) are isolated from lymphocytes using techniques known to a person or ordinary skill in the art including, for example, commercially available kits from STEMCELL Technologies, Inc., Miltenyi Biotec, Inc., and Thermo Fisher Scientific, Inc.

In some embodiments, B-cells or a subpopulation of B-cells from a subject(s) are used to make a library of antigen binding domains. In some embodiments, nucleic acids encoding the light and heavy chain of the antigen binding domain are amplified from either (or both) the genomic DNA of the B-cells (or subpopulation of B-cells) and/or the mRNA of the B-cells (or subpopulation of B-cells). Techniques and primers for amplifying nucleic acids encoding human antibody light and heavy chains are well-known in the art, and described in, for example, Pro-Gen's Human IgG and IgM Library Primer Set, Catalog No. F2000; Andris-Widhopf et al., "Generation of Human Fab Antibody Libraries: PCR Amplification and Assembly of Light and Heavy Chain Coding Sequences," Cold Spring Harb. Protoc. 2011; Lim et al., Nat. Biotechnol. 31:108-117 (2010); Sun et al., World J. Microbiol. Biotechnol. 28:381-386 (2012); Coronella et al., Nucl. Acids. Res. 28:e85 (2000), all of which are incorporated by reference in their entirety for all purposes. Techniques and primers for amplifying nucleic acids encoding mouse antibody light and heavy chains are well-known in the art, and described in, for example, U.S. Pat. No. 8,143,007; Wang et al., BMC Bioinform. 7(Suppl):S9 (2006), both of which are incorporated by reference in their entirety for all purposes. In some embodiments, the antibody repertoires are used as separate chains in antigen binding domains, or converted to single chain antigen binding domains. In some embodiments, single chain antibodies are made from nucleic acids encoding human light and heavy chains using techniques well-known in the art including, for example, those described in Pansri et al., BMC Biotechnol. 9:6 (2009); Peraldi-Roux, Methods Molc. Biol. 907:73-83 (2012), both of which are incorporated by reference in their entirety for all purposes. In some embodiments, single chain antibodies are made from nucleic acids encoding mouse light and heavy chains using techniques well-known in the art including, for example, those described in Imai et al., Biol. Pharm. Bull.

29:1325-1330 (2006); Cheng et al., PLoS ONE 6:e27406 (2011), both of which are incorporated by reference in their entirety for all purposes.

In some embodiments, T-cells or a subpopulation of T-cells from a subject(s) are used to make a library of antigen binding domains. In some embodiments, nucleic acids encoding T-cell receptors are amplified from either (or both) the genomic DNA of the T-cells (or subpopulation of T-cells) and/or the mRNA of the T-cells (or subpopulation of T-cells). Techniques and primers for amplifying nucleic acids encoding the T-cell receptors from lymphocytes are well known in the art and are described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. In some embodiments, the TCR repertoires are used as separate chains to form an antigen binding domain. In some embodiments, the TCR repertoires are converted to single chain antigen binding domains. In some embodiments, single chain TCRs are made from nucleic acids encoding human alpha and beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/Aggen David.pdf?sequence=1, all of which are incorporated by reference in their entirety for all purposes.

In some embodiments, natural killer cells, dendritic cells, macrophages, T-cells, and/or B-cells are used to make a library of NKG receptor binding domains and/or Toll-like receptor binding domains. In some embodiments, the natural killer cells, dendritic cells, macrophages, T-cells, and/or B-cells are obtained from a subject who has become immune to a disease or has had an immune response to a disease or condition. In some embodiments, the antigen binding domains from the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105), and/or innate immunity receptors are obtained from the subjects immune cells (natural killer cells, dendritic cells, macrophages, T-cells, and B-cells). In some embodiments, the extracellular elements for the library are made as described in U.S. Pat. Nos. 5,359,046, 5,686,281 and 6,103,521 (which are hereby incorporated by reference in their entirety for all purposes). In some embodiments, the extracellular element is part of a receptor which is monomeric, homodimeric, heterodimeric, or associated with a larger number of proteins in a non-covalent complex. In some embodiments, a multimeric receptor has only one polypeptide chain with a major role in binding to the ligand. In these embodiments, the extracellular element can be derived from the polypeptide chain that binds the ligand. In some embodiments, the receptor is a complex of extracellular portions from several proteins that forms covalent bonds through disulfide linkages. In this embodiment, the extracellular element of the CAR may also form such multimeric extracellular complexes. In some embodiments, the extracellular element is comprised of truncated portions of the receptor, where such truncated portion is functional for binding ligand.

In some embodiments, nucleic acids encoding the antibody repertoire from B-cells or subpopulations of B-cells from a subject are used as the antigen binding domain for CAR chassis, Smart CAR chassis, DE-CAR chassis, Smart-DE-CAR chassis, or Side CAR chassis. In some embodiments, nucleic acids encoding single chain antibodies obtained by combinatorial pairing of the nucleic acids encoding the light and heavy chains of antibodies from the B-cells or subpopulations of B-cells from a subject are combined with the CAR chassis, Smart CAR chassis, DE-CAR chassis, Smart-DE-CAR chassis, or Side CAR chassis. In some embodiments, the library of CARs, Smart CARs, DE-CARs, Smart-DE-CARS, or Side CARs made with the antibody repertoire are placed into eukaryotic cells (e.g., lymphocytes) to make a library of eukaryotic cells with the library of CARs, Smart CARs, DE-CARs, Smart-DE-CARS, or Side CARs.

In some embodiments, nucleic acids encoding the T-cell receptor repertoire from T-cells or subpopulations of T-cells from a subject are used as the antigen binding domain for CAR chassis, Smart CAR chassis, DE-CAR chassis, Smart-DE-CAR chassis, or Side CAR chassis. In some embodiments, nucleic acids encoding single chain TCRs obtained by combinatorial pairing of the nucleic acids encoding the alpha and beta chains of TCRs from the T-cells or subpopulations of T-cells from a subject are combined with the CAR chassis, Smart CAR chassis, DE-CAR chassis, Smart-DE-CAR chassis, or Side CAR chassis. In some embodiments, the library of CARs, Smart CARs, DE-CARs, Smart-DE-CARS, or Side CARs made with the T-cell receptor repertoire are placed into eukaryotic cells (e.g., lymphocytes) to make a library of eukaryotic cells with the library of CARs, Smart CARs, DE-CARs, Smart-DE-CARS, or Side CARs.

In some embodiments, this library of eukaryotic cells is challenged with an antigen and eukaryotic cells with a CAR, Smart CAR, DE-CAR, Smart-DE-CAR or Side CAR that have an antigen binding domain that interacts with the antigen can be stimulated to proliferate. In some embodiments, the antigen binding domains with the strongest binding to the antigen will proliferate best, and so this challenge with antigen will select for CARs, Smart CARs, DE-CARs, Smart-DE-CARS, or Side CARs that bind to the antigen, and those CARs, Smart CARs, DE-CARs, Smart-DE-CARS, or Side CARs which bind strongly to the antigen may proliferate best. In some embodiments, the antigen challenge produces antigen binding domains that will bind the antigen. In some embodiments, the antigen challenge is done with a tumor associated antigen and this produces CAR, Smart CAR, DE-CAR, Smart-DE-CAR, and/or Side CAR constructs that can be used in a cancer and/or tumor therapy. In some embodiments, the antigen challenge is done with an antigen from an infectious disease and this produces CAR, Smart CAR, DE-CAR, Smart-DE-CAR, and/or Side CAR constructs that can be used in therapies to treat the infectious disease. In some embodiments, the antigen challenge is done with an antigen from a cell infected with a virus and this produces CAR, Smart CAR, DE-CAR, Smart-DE-CAR, and/or Side CAR constructs that can be used in therapies to treat infection by the virus.

In some embodiments, eukaryotic cell further comprises a reporter that produces a detectable signal when the CAR, DE-CAR, and/or Side-CAR polypeptide is activated by antigen. In some embodiments, binding of antigen by the CAR, DE-CAR, and/or Side-CAR polypeptide activates the T-cell and this activation induces expression of the reporter from a reporter gene that is operably linked to an NFAT control region. In some embodiments, activation of the CAR produces a second messenger that activates a control region linked to a reporter gene or binds to a RNA control device or DE that controls the expression of the reporter. In some embodiments, binding of antigen by the CAR, DE-CAR, and/or Side-CAR polypeptide leads to the phosphorylation of other polypeptides in the eukaryotic cell. In some embodiments, the reporter is activated by phosphorylation. In some embodiments, the reporter is indirectly activated by phosphorylation of a polypeptide. In some embodiments, the signal produced from the reporter is used as a measure of antigen interaction with the antigen binding domain, and for example, positive reporter signal may be used to identify antigen binding domains that can bind to an antigen. In some embodiments, the reporter is an optical reporter (e.g., a bioluminescent protein such as luciferase or a fluorescent protein such as GFP) and eukaryotic cells showing an optical signal above a threshold amount (indicating a threshold degree of binding of antigen by the antigen binding domain) are identified. In some embodiments, the threshold amount of optical activity is measured by a fluorescence activated cell sorter, such as those commercially sold by Becton Dickinson Biosciences, ThermoFisher, and Beckman Coulter. In some embodiments, FACs is used to separate cells with antigen binding domains that interact with antigen from those cells that do not interact with antigen.

In some embodiments, the CAR, Smart CAR, DE-CAR, Smart-DE-CAR, and/or Side CAR constructs obtained in the antigen challenge are challenged with antigen for one or more cycles. In some embodiments, the subsequent challenges with antigen further select for antigen binding domains that bind to the antigen and/or further enriches for antigen binding domains with higher affinity for the antigen. In some embodiments, ligand for the Smart CAR, DE-CAR, Smart-DE-CAR, and/or Side CAR is/are changed during subsequent challenges so that the amount of CAR, DE-CAR, and/or operable Side CAR in the eukaryotic cells is decreased. In some embodiments, decreasing the amount of CAR, DE-CAR, and/or operable Side CAR in the cells can select for antigen binding domains having greater affinity for the antigen.

In some embodiments, an antigen binding domain is given random or directed changes in the CDRs and associated sequences and subsequent challenges with antigen select and/or enrich for increased affinity in binding to the antigen. In some embodiments, the ligand for the Smart CAR, DE-CAR, Smart-DE-CAR, and/or Side CAR is/are changed during subsequent challenges so that the amount of CAR, DE-CAR, and/or operable Side CAR in the eukaryotic cells is decreased. In some embodiments, decreasing the amount of CAR, DE-CAR, and/or operable Side CAR in the cells can select for antigen binding domains with greater affinity for the antigen. In some embodiments, this affinity maturation of the antigen binding domains can increase the affinity for antigen by the antigen binding domain to a desired level.

In some embodiments, clones are obtained from the eukaryotic cells with the library of CAR, Smart-CAR, DE-CAR, SMART-DE-CAR, and/or Side CAR constructs. In some embodiments, the nucleic acids encoding the antigen binding domain form the clone are amplified or cut out of the nucleic acid encoding the CAR, Smart-CAR, DE-CAR, SMART-DE-CAR, and/or Side CAR and cloned into a suitable recombinant vector for expression of the antigen binding domain. In some embodiments, the selected antigen binding domains are sequenced. In some embodiments, the selected antigen binding domains are expressed, purified and characterized for binding to the target antigen. In some embodiments, these antigen binding domains are used in therapies to treat the disease associated with the target antigen.

Identification of Target Antigen for the New Antigen Binding Domains

In some embodiments, the new antigen binding domains are identified using impure fractions or whole cells (or whole virus) as targets for the CAR, Smart CAR, DE-CAR, Smart-DE-CAR, and/or Side CAR libraries. In some embodiments, the whole cells may be diseased cells (e.g., cancer cells or cells infected with a pathogen) or healthy cells. In some embodiments, techniques well known in the art are used to enrich and/or purify the target antigen from the whole cells (or whole virus) or impure fractions, including, for example, electrophoretic, molecular, immunological and chromatographic techniques, including ion exchange, hydrophobic, affinity, and reverse-phase HPLC chromatography, and chromatofocusing. Protein Purification: Principles and Practice, Springer Science and Business Media, $3^{rd}$ Edition (1994); Molecular Cloning A Laboratory Manual, 2nd Ed., ed. by Sambrook, Fritsch and Maniatis (Cold Spring Harbor Laboratory Press: 1989); Ausubel et al., Eds Short Protocols in Molecular Biology (5th Ed. 2002); DNA Cloning, Volumes I and II (D. N. Glover ed., 1985), all of which are incorporated by reference in their entirety for all purposes. In some embodiments, the antigen binding domain is used to purify the antigen using affinity techniques, e.g., an antigen binding domain column for affinity chromatography, precipitation of the antigen from a sample using the antigen binding domain, or attachment of the antigen binding domain to beads (e.g., magnetic beads) for separation of the antigen from a sample.

In some embodiments, the fractions obtained from the purification steps are tested for binding by the antigen binding domains. In some embodiments, binding by the antigen binding domain to the target antigen is detected by methods well known in the art, including, for example, FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration.

In some embodiments, the above methods provide pairs of antigen binding domains together with validated target antigens. In some embodiments, the target antigen is a polypeptide or a modified polypeptide (e.g., glycosylated). In some embodiments, the polypeptide is subjected to analysis to determine its amino acid composition, and its amino acid sequence using, for example, techniques and services available commercially from Bioproximity, LLC, Alphalyse, Inc., and Applied Biomics, Inc. In some embodiments, the polypeptide sequence obtained for the target antigen is used to identify the gene encoding the polypeptide from known gene sequences found at, for example, the National Center for Biotechnology Information. In some embodiments, the gene encoding the target antigen is not found in available databases, and the polypeptide sequence information is used to clone the gene encoding the target antigen using techniques well known in the art including, for example, those taught in Maniatis (Cold Spring Harbor Laboratory Press: 1989); Ausubel et al., Eds Short Protocols in Molecular Biology (5th Ed. 2002), which are incorporated by reference in their entirety for all purposes.

In some embodiments, further validation is performed to show that the identified target antigen is enriched on target cells compared to healthy tissue in subjects. In some embodiments, the target antigens are characterized to show that a therapeutic effect is obtained when the subject is treated with antigen binding domains (e.g., antibody drug conjugates) and/or cells with Smart CAR, DE-CAR, Smart-DE-CAR, and/or Side CARs specific for the target antigen.

Uses of Eukaryotic Cells with Smart CAR, DE-CAR, Smart-DE-CAR, and/or Side CAR

In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in eukaryotic cells. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in mammalian cells. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in human cells or murine cells. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptide in hematopoietic cells. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in T-cells, natural killer cells, B-cells, or macrophages. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in T-cells or natural killer cells.

In some embodiments, the nucleic acids encoding the Smart CAR(s), DE-CAR(s), Smart-DE-CAR(s), and/or Side CAR(s) of the invention are used to express a desired level of CAR, DE-CAR, and/or Side-CAR polypeptide on the surface of the eukaryotic cell. In this embodiment, the DE, RNA control device, and/or Side-CAR controls the level of CAR, DE-CAR, and/or Side-CAR polypeptide expression, at least in part, and by modulating the level of activity of the DE, RNA control device, and/or Side-CAR, a desired amount of CAR, DE-CAR, and/or Side-CAR polypeptide is expressed and displayed on the surface of the eukaryotic cell. In some embodiments, the DE increases the degradation rate of DE-CAR polypeptide in the eukaryotic cell and when ligand is bound by the DE, the rate of degradation decreases. In some embodiments, the DE increases degradation of the DE-CAR polypeptide when ligand is bound by the DE. In some embodiments, the RNA control device inhibits translation of the DE-CAR mRNA and when ligand binds to the sensor element of the RNA control device this inhibition of translation is reduced so that DE-CAR polypeptide expression is increased. In some embodiments, ligand for the Side-CAR causes the two Side-CAR polypeptides to form an active CAR. In some embodiments, ligand for the DE, the ligand for the RNA control device sensor, and/or the ligand for the Side-CAR is added in increasing amounts to the eukaryotic cells with the Smart CAR(s), DE-CAR(s), Smart-DE-CAR(s), and/or Side CAR(s) until a desired level of CAR, DE-CAR, and/or Side-CAR polypeptide is made in the eukaryotic cell. In some embodiments, the amount of CAR, DE-CAR, and/or Side-CAR polypeptide is measured using antibodies specific for the CAR, DE-CAR, and/or Side-CAR polypeptide. In some embodiments, the amount of CAR, DE-CAR, and/or Side-CAR polypeptide is measured using the antigen recognized by the extracellular element. In some embodiments, the amount of CAR, DE-CAR, and/or Side-CAR polypeptide is measured in a functional assay of target cell killing. In some embodiments, the amount of CAR, DE-CAR, and/or Side-CAR polypeptide is measured in a functional assay for eukaryotic cell proliferation (induced by the CAR, DE-CAR, and/or Side-CAR polypeptide). In some embodiments, the above eukaryotic cell is a T-lymphocyte or a natural killer cell or a macrophage or other phagocytic cell type.

In some embodiments, the ligand for the DE, the ligand for the RNA control device sensor, and/or the ligand for the Side-CAR is added in increasing amounts until a desired level of eukaryotic cell activity is obtained. In some embodiments, the desired eukaryotic cell activity is killing of a target cell. In some embodiments, target cell killing occurs over a desired time period, e.g., the killing of a certain number of target cells in 12 hours, or 24 hours, or 36 hours, or two days, or 3, 4, 5, 6, 7, 8, 9, 10, 11, 12, 13, 14, 15, 16, 17, 18, 19, 20, 21, 22, 23, 24, 25, 26, 27, or 28 days, or two months, or 3, 4, 5, or 6 months. In some embodiments, target cell killing is expressed as a half-life for a standardized number of target cells. In this embodiment, the half-life of target cell killing can be 12 hours, 24 hours, 36 hours, or 2, 3, 4, 5, 6, 7, 8, 9, 10, 11, 12, 13, 14, 15, 16, 17, 18, 19, 20, 21, 22, 23, 24, 25, 26, 27, or 28 days, or two months, or 3, 4, 5, or 6 months. In some embodiments, the desired eukaryotic cell activity is proliferation. In some embodiments, the cell proliferation occurs with a doubling time of 12 hours, 24 hours, 36 hours, two days, or 3, 4, 5, 6, or 7 days. In some embodiments, the above eukaryotic cell is a T-lymphocyte or a natural killer cell or a macrophage or other phagocytic cell type.

In some embodiments, a regime of different amounts of ligand (for the sensor, DE, and/or Side-CAR) is added over time so that different desired levels of CAR, DE-CAR, and/or Side-CAR polypeptide are present on the eukaryotic cell at different times. For example, during the enrichment/selection of antigen binding domains with Smart CAR, DE-CAR, Smart-DE-CAR, and/or Side CAR T-cells or Smart CAR, DE-CAR, Smart-DE-CAR, and/or Side CAR natural killer cells, the amount of CAR, DE-CAR, and/or Side-CAR polypeptide expression may be relatively high initially to ensure that some antigen binding domains are able to bind target antigen, and in subsequent rounds of enrichment/selection, the amount of CAR, DE-CAR, and/or Side-CAR polypeptide expression can be decreased to enrich/select for antigen binding domains with higher affinity for target antigen. In some embodiments, the CAR, DE-CAR, and/or Side-CAR polypeptide expression may be relatively low initially to enrich/select for antigen binding domains that bind tightly to the target antigen, and in subsequent rounds CAR, DE-CAR, and/or Side-CAR polypeptide expression level is increased to increase the proliferation rate of the clones with antigen binding domains that bind target antigen.

In some embodiments the nucleic acid sequences encoding a cognate RNA control device or devices are present in a nucleic acid locus encoding a chimeric antigen receptor transgene. In some embodiments, RNA control devices are encoded for as nucleic acid sequence in the vector proximal, distal, or within the ORF encoding a CAR, DE-CAR, and/or Side-CAR polypeptide. An example of a schematic of a vector is included in FIG. 1, adapted from (Budde et al., PLoS1, 2013, doi:10.1371/journal.pone.0082742, which is incorporated by reference in its entirety for all purposes). In some embodiments nucleic acid sequences encoding an RNA control device or devices are located within the 3' UTR region of the transgene. In some embodiments nucleic acid sequences encoding an RNA control device or devices are located in the 5' UTR region of the DE-CAR transgene. In some embodiments nucleic acid sequences encoding an RNA control device or devices are located within synthetic or natural introns flanked by coding or noncoding exons within the CAR transgene, or at intron/exon boundaries.

Other uses of the CAR, Smart CAR, DE-CAR, Smart-DE-CAR, Side CAR and/or universal-CARs of the invention are described in U.S. patent application Ser. No. 15/070,352 filed on Mar. 15, 2016, which is incorporated by reference in its entirety for all purposes. For example, U.S. Ser. No. 15/070,352 describes the used of multiple TAA targets, multiple DE and/or RNA control devices for a CAR, and universal CARs. The use of RNA control devices and/or DEs with other genes in eukaryotic cells expressing CAR, Smart CAR, DE-CAR, Smart-DE-CAR, Side CAR and/or universal-CARs of the invention is also described in U.S. patent application Ser. No. 15/070,352 filed on Mar. 15, 2016, which is incorporated by reference in its entirety for all purposes.

Target Cell Killing Assay

In some embodiments, methods are used to measure target cell killing after the addition of a cell killing agent. In some embodiments, the cell killing agent is, for example, a host cell with a CAR device, Smart CAR device, DE CAR device, Smart-DE CAR device, and/or Side-CAR devices, a small molecule agent, a biological agent (e.g., an antibody, a cytokine, an antibody-drug conjugate, etc.), a small molecule drug conjugate, or a nanoparticle-drug conjugate. In some embodiments, the target cell is modified to contain a reporter that is released when the target cell is killed. In some embodiments, the reporter is an optical reporter, an enzyme (e.g., β-galactosidase, alkaline phosphatase, chloramphenicol acetyltransferase, horseradish peroxidase, β-lactamase), a fluorescent reporter (e.g., GFP, RFP), a bioluminescent reporter (e.g., luciferase), or another reporter. In some embodiments, the target cell is a mammalian cell, a mouse cell, a rat cell, a human cell, a bacterial cell, or a fungal cell. In some embodiments, the target cell is a diseased cell, such as for example, a cancer cell, or a cell infected with a bacterial, fungal, and/or viral pathogen.

In some embodiments, a target cell killing assay is used for quality control and quality assurance in the making of a host cell containing a CAR device, Smart CAR device, DE CAR device, Smart-DE CAR device, and/or Side-CAR devices. In some embodiments, the target cell killing assay of the invention is used to define part of a specification for a host cell containing a CAR device, Smart CAR device, DE CAR device, Smart-DE CAR device, and/or Side-CAR devices for the treatment of certain diseases. In some embodiments, the cell killing assay of the invention is used to engineer parts of a CAR device, Smart CAR device, DE CAR device, Smart-DE CAR device, and/or Side-CAR devices. In some embodiments, the cell killing assay of the invention is used in a screening assay to identify clones with more or less activity.

In some embodiments, the target cell is made to express a reporter by engineering a reporter gene into the target cell. In some embodiments, the reporter gene is inserted into a safe harbor site of the target cell. In some embodiments, the reporter gene is inserted into a desired site of the target cell that produces a phenotype in addition to the reporter phenotype. In some embodiments, the reporter gene is transiently engineered into the target cell (e.g., plasmid borne). In some embodiments, the reporter gene is under the control of a constitutive control region. In some embodiments, constitutive control regions include, for example, the cytomegalovirus (CMV) control region, simian virus 40 (SV40) early control region, mouse mammary tumor virus (MMTV), human immunodeficiency virus (HIV) long terminal repeat (LTR) control region, MoMuLV control region, an avian leukemia virus control region, an Epstein-Barr virus immediate early control region, a Rous sarcoma virus control region, as well as human control regions such as, but not limited to, the actin control region, the myosin control region, the elongation factor-1a control region, the hemoglobin control region, and the creatine kinase control region. In some embodiments, the reporter gene is under the control of an inducible control region. In some embodiments, the inducible control regions include, for example, a metallothionein control region, a glucocorticoid control region, a progesterone control region, a tetracycline control region, a c-fos control region, the T-REx system of ThermoFisher which places expression from the human cytomegalovirus immediate-early control region under the control of tetracycline operator(s), and the RheoSwitch control regions of Intrexon.

In some embodiments, the target cell is modified to contain a reporter gene using CRISPR/Cas9, TALEN, Zinc-Finger Nuclease, or equivalent systems. In some embodiments, the reporter gene is inserted at a safe harbor site within the target cell. In some embodiments, the construct carrying the reporter gene includes a selectable marker that is also inserted at a safe harbor site of the target cell. In some embodiments, the selectable marker is used to select for target cells that have been modified with the reporter gene construct. In some embodiments, the reporter gene is inserted at the locus for a cell surface antigen recognized by a CAR, DE-CAR, and/or Side-CAR polypeptide(s). In some embodiments, the reporter gene is inserted at both alleles for a cell surface antigen recognized by a CAR, DE-CAR, and/or Side-CAR polypeptide(s). In some embodiments, the reporter gene inserted at the cell surface antigen allele is different from the reporter gene inserted at a different site in other target cells. In some embodiments, the target cells with a reporter gene inserted at the cell surface antigen allele are used as a control for the cell killing assay.

In some embodiments, the target cell is an adherent cell and the reporter gene is stably integrated into a chromosome of the target cell. In some embodiments, target cells are grown into a monolayer and then exposed to a cell killing agent including, for example, host cells with a CAR device, Smart CAR device, DE CAR device, Smart-DE CAR device, and/or Side-CAR devices. When the cell killing agent lyses a target cell the reporter contained therein is released into the cell media. The released reporter can then be measured to determine the amount of target cell killing. In some embodiments, the reporter is measured in the cell media while the cell killing is occurring. In some embodiments, the measurements of reporter are made in real time. In some embodiments, the reporter interacts with reagents to make the detected signal. In some embodiments, the reagents are impermeable or poorly permeable to the cell membrane of the target cells. In these embodiments, the target cells do not need to be removed from the solution to measure reporter released by cell killing. In some embodiments, reporter measurements are performed on the well with the adherent target cells in a manner that excludes the adherent target cells from the measurement. For example, if the adherent layer of target cells is at the bottom of the well, reporter measurements could be taken through the well above the adherent cells. In some embodiments, these measurements are performed in real time. In some embodiments, the reporter is an optical reporter and the optical reading device measures the reporter in the media by reading a section of container that does not include the monolayer of target cells.

In some embodiments, the target cell is a suspension cell with the reporter gene stably integrated into a chromosome of the target cell. In this embodiment, the target cells are prepared at a certain density and then combined with a cell killing agent including, for example, host cells containing CAR device, Smart CAR device, DE CAR device, Smart-DE CAR device, and/or Side-CAR devices. When the cell killing agent lyses a target cell the reporter contained therein is released into the cell media. The released reporter can then be measured to determine the amount of target cell killing. If reagents for the reporter are impermeable or poorly permeable to the target cell membrane, then measurements of the reporter released from the target cells may be performed directly on the solution with the target cells. In some embodiments, these measurements of reporter are performed in real time. In some embodiments, the solution with the target cells is subjected to a treatment to separate the live targets from the reporter in solution. After this treatment, the reporter in the solution may be measured.

In some embodiments, the reporter is an enzyme and the reagents that interact with the enzyme to produce the detectable signal are impermeable to the target cell membrane. In this embodiment, the measurement of the reporter can occur in the presence of target cells as only reporter that has been released by target cells will be measured. In some embodiments, the reporter reacts with another agent to be detected and this agent is impermeable to the target cell membrane. In this embodiment, the measurement of reporter can occur in the presence of target cells because the agent which detects the reporter can only react with reporter that has been released by the target cells. In some embodiments, the media is separated from the target cells, and optionally the host cells with the CAR device, Smart CAR device, DE CAR device, Smart-DE CAR device, and/or Side-CAR devices, and then the reporter is measured in the separated media.

In some embodiments, the host cell for the CAR device, Smart CAR device, DE CAR device, Smart-DE CAR device, and/or Side-CAR devices is also engineered with a reporter gene. In some embodiments, the host cell is engineered with a different reporter gene than that engineered into the target cell. In some embodiments, the reporter engineered into the host cells is measured and used to normalize the signal from the reporter released from the lysed target cells. In some embodiments, the reporter in the killing cell is used to measure the amount of killing cells added to the target cells in the target cell killing assay. In some embodiments, the killing cell is a T-lymphocyte, a natural killer cell, or a B-lymphocyte. In some embodiments, the killing cell contains a CAR device, Smart CAR device, DE CAR device, Smart-DE CAR device, and/or Side-CAR device. In some embodiments, the reporter in the killing cell is secreted from the killing cell. In this embodiment, the amount of reporter secreted can correlate with the quantity of killing cells. In some embodiments, the different reporter engineered into the host cell is detected separately from the reporter released from the target cells. In some embodiments, the target cell and control cell or a different target cell have different reporters engineered into the cells.

The two or more reporters could be fluorescent and/or luminescent proteins that produce light at different wavelengths. Such paired light producing reporters are commercially available from ThermoFisher Scientific as dual-spectral luciferase pairs for multiplex detection. For example, among other combinations, ThermoFisher Scientific multiplexes Red Firefly luciferase (640 nm) with *Renilla* luciferase (460 nm), Red Firefly luciferase (640 nm) with Green *Renilla* luciferase (525 nm), *Gaussia* luciferase (470 nm) with Red Firefly luciferase (640 nm), or *Cypridina* luciferase (470 nm) with Red Firefly luciferase (640 nm). In some embodiments, the host cell is engineered with an enzyme reporter that is paired with a cell membrane permeable substrate that produces light at a different wavelength from the reporter used in the target cells. In these embodiments, the tested sample(s) is subjected to different conditions that activate the reporters from the target cell and/or host cell to produce signal, and those signals are measured. In some embodiments, a fluorescent protein is used as a reporter in the host cell and a bioluminescent protein is used as the reporter in the target cell. In some embodiments, the reporters are measured separately, and in some embodiments, the reporters are measured at the same time.

In some embodiments, another cell is engineered with a different reporter gene for the cell killing assay. In some embodiments, this other cell is a control cell, for example, if the target cell is a cancerous cell, the control cell can be a normal tissue cell, or a cancer cell in which the antigen target for the CAR device, Smart CAR device, DE CAR device, Smart-DE CAR device, and/or Side-CAR devices has been knocked out by a double allele knockout. In some embodiments, the target cell is a diseased cell, and the control cell is a normal tissue cell. In some embodiments, a cell killing agent, including, for example, host cells with CAR device, Smart CAR device, DE CAR device, Smart-DE CAR device, and/or Side-CAR devices, is added to the target cells and control cells and after a specific time period the reporters from the target cells and control cells are measured. In some embodiments, this dual reporter data will provide a measure of the specificity of target cell killing.

Target Cells

Target cells can be any cell type including eukaryotic cells or prokaryotic cells. In some embodiments, target cells are mammalian cells, such as, for example mouse cells, rat cells, dog cells, cat cells, or human cells. In some embodiments, target cells include, for example, cancer cells, tumor cells, hematopoietic cells, inflammatory cells, cardiovascular cells, pancreatic cells, cells from other organs in a mammal, or cells infected by a viral, bacterial, fungal, or protozoan pathogen.

In some embodiments, the target cell is a cancer cell. In some embodiments, the cancer cell is a sarcoma, carcinoma, melanoma, chordoma, malignant histiocytoma, mesothelioma, glioblastoma, neuroblastoma, medulloblastoma, malignant meningioma, malignant schwannoma, leukemia, lymphoma, myeloma, myelodysplastic syndrome, myeloproliferative disease. In some embodiments, the cancer cell expresses one or more of the antigens 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNTO888, CTLA-4, DR5, EGFR, EpCAM, CD3, FAP, fibronectin extra domain-B, folate receptor 1, GD2, GD3 ganglioside, glycoprotein 75, GPNMB, HER2/ neu, HGF, human scatter factor receptor kinase, IGF-1 receptor, IGF-I, IgG1, L1-CAM, IL-13, IL-6, insulin-like growth factor I receptor, alpha 5β1-integrin, integrin αvβ3, MORAb-009, MS4A1, MUC1, mucin CanAg, N-glycolyl-neuraminic acid, NPC-1C, PDGF-Rα, PDL192, phosphatidylserine, prostatic carcinoma cells, RANKL, RON, ROR1, SCH 900105, SDC1, SLAMF7, TAG-72, tenascin C, TGF β2, TGF-β, TRAIL-R1, TRAIL-R2, tumor antigen CTAA16.88, VEGF-A, VEGFR-1, VEGFR2, 707-AP, ART-4, B7H4, BAGE, β-catenin/m, Bcr-abl, MN/C IX antibody, CAMEL, CAP-1, CASP-8, CD25, CDC27/m, CDK4/m, CT, Cyp-B, DAM, ErbB3, ELF2M, EMMPRIN, EphA3, ETV6-AML1, G250, GAGE, GnT-V, Gp100, HAGE, HLA-A*0201-R170I, HPV-E7, HSP70-2M, HST-2, hTERT (or hTRT), iCE, IL-2R, IL-5, KIAA0205, LAGE, LDLR/FUT, MAGE, MART-1/melan-A, MART-2/Ski, MC1R, myosin/m, MUM-1, MUM-2, MUM-3, NA88-A, PAP, proteinase-3, p190 minor bcr-abl, Pml/RARα, PRAME, PSA, PSM, PSMA, RAGE, RU1 or RU2, SAGE, SART-1 or SART-3, survivin, TPI/m, TRP-1, TRP-2, TRP-2/INT2, WT1, NY-Eso-1 or NY-Eso-B or vimentin.

In some embodiments, the target cell is a cell involved in an inflammatory disease and the cell expresses one of more of the antigens, including, for example, AOC3 (VAP-1), CAM-3001, CCL11 (eotaxin-1), CD125, CD147 (basigin), CD154 (CD40L), CD2, CD20, CD23 (IgE receptor), CD25 (α-chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, Lama glama, LFA-1 (CD11 a), MEDI-528, myostatin, OX-40, rhuMAb .beta.7, scleroscin, SOST, TGF β1, TNF-α or VEGF-A.

In some embodiments, the target cell is from a neuronal disorder expressing one or more of beta amyloid or MABT5102A. In some embodiments, the target cell is involved in diabetes and expressed one or more of L-1β or CD3. In some embodiments, the target cells is from a cardiovascular disease expressing one or more of C5, cardiac myosin, CD41 (integrin α-IIb), fibrin II, beta chain, ITGB2 (CD18) and sphingosine-1-phosphate.

In some embodiments, the target cell is a *Chlamydophila* (*Chlamydia*), *Ehrlichia*, *Rickettsia*, *Neisseria*, *Brucella*, *Mycobacterium*, *Listeria*, *Francisella*, *Legionella*, *Yersinia*, *Nocardia*, *Rhodococcus*, *Coxiella*, *Staphylococci*, *Streptococcus*, *Escherichia coli*, *Pseudomonas*, or *Salmonella*. In some embodiments, the target cell is a mammalian cell infected with one of the foregoing bacteria. In some embodiments, the target cell is *Staphylococcus aureus*, *Neisseria gonorrhoeae*, *Streptococcus pyogenes*, Group A *Streptococcus*, Group B *Streptococcus* (*Streptococcus agalactiae*), *Streptococcus pneumoniae*, and *Clostridium tetani*. In some embodiments, the target cell is an infectious pathogen. In some embodiments, the target cell is infected with an infectious pathogen (e.g., a virus, a bacteria, a protozoan, or a fungus). In some embodiments, target cells are infected with bacterial pathogens including, for example, *Helicobacter pyloris*, *Legionella pneumophilia*, a bacterial strain of *Mycobacteria* spp. (e.g. *M. tuberculosis*, *M. avium*, *M. intracellulare*, *M. kansaii*, or *M. gordonea*), *Neisseria meningitides*, *Listeria monocytogenes*, *R. rickettsia*, *Salmonella* spp., *Brucella* spp., *Shigella* spp., or certain *E. coli* strains or other bacteria that have acquired genes with invasive factors. In some embodiments, the pathogen is a eukaryote including, for example, a *Histoplasma*, *Cryptococcus*, *Trypanosoma*, Apicomplexans (e.g., *Plasmodium*), and/or *Pneumocystis*. In some embodiments, target cells are infected with viral pathogens including, for example, Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

In some embodiments, the target cell is involved in a hematopoietic disorder such as a malignancy or an autoimmune disease. In some embodiments, the cell is a leukemia cell, lymphoma cell, myeloma cell, or sarcoma cell. In some embodiments, the target cell is a multiple myeloma cell. In some embodiments, the target cell is a CD19 and/or CD20 positive B-cell. In some embodiments, the leukemia cells include, for example, acute lymphoblastic leukemia cells (ALL), acute myelogenous leukemia cells (AML), chronic lymphocytic leukemia cells (CLL), chronic myelogenous leukemia cells (CML), acute monocytic leukemia cells (AMoL), B-cell prolymphocytic leukemia cells, Hairy cell leukemia cells, T-cell prolymphocytic leukemia cells, T-cell large granular lymphocytic leukemia cells, and NK-cell leukemia cells. In some embodiments, lymphoma target cells include, for example, Hodgkin's lymphoma cells, Non-Hodgkin's lymphoma cells, lymphoplasmacytic lymphoma cells, Splenic marginal zone lymphoma cells, small B-cell lymphoma cells, Waldenström macroglobulinemia cells, MALT lymphoma cells, Nodal marginal zone lymphoma cells, Pediatric follicular lymphoma cells, Mantle cell lymphoma cells, Diffuse large B-cell lymphoma cells (DLBCL), large B-cell lymphoma cells, Plasmablastic lymphoma cells, Burkitt lymphoma cells, and T-cell lymphoma cells. In some embodiments, myeloma target cells include, for example, multiple myeloma cells, and plasma cell myeloma cells. In some embodiments, sarcoma target cells include, for example, Histiocytic sarcoma cells, dendritic cell sarcoma cells, and Langerhans cell sarcoma cells.

In some embodiments, the target cell is from an acute myeloid leukemia (AML) expressing antigens including but not limited to any one or more of CD 33, CD 34, CD 38, CD 44, CD 45, CD 45RA, CD 47, CD 64, CD 66, CD 123, CD 133, CD 157, CLL-1, CXCR4, LeY, PR1, RHAMM (CD 168), TIM-3, and/or WT1. In some embodiments, the target cell is from a B-cell malignancy expressing antigens including, for example, CD5, CD 10, CD 19, CD 20, CD 21, CD 22, CD 23, CD 43, and CD79a. In some embodiments, target cells are from T-cell malignancies expressing antigens including, for example, CD2, CD3, CD4, CD5, CD7, and CD8. In some embodiments, target cells are from NK cell malignancies expressing antigens including, for example, CD 16 and CD 56. In some embodiments, target cells are from other myeloid malignancies expressing antigens including, for example, CD13, CD33, CD 38, and CD117. In some embodiments, target cells are from dendritic cell malignancies expressing antigens including, for example, CD 11c and CD123. In some embodiments, target cells are monocyte malignancies expressing antigens including, for example, CD 14 and CD 33.

In some embodiments, target cells are from hairy cell leukemias expressing antigens including, for example, CD 11, CD 19, CD 22, CD 25, and CD 103. In some embodiments, target cells are from splenic marginal zone lymphoma expressing antigens including, for example, CD19, CD22, and FMC7. In some embodiments, target cells are from lymphoplasmacytic lymphoma expressing antigens including, for example, B19, FMC7, and CD38. In some embodiments, target cells are from follicular lymphoma expressing antigens including, for example, CD19, CD22, CD23, and CD10. In some embodiments, target cells are hematopoietic stem cells expressing antigens including, for example, CD 34, CD 41, CD 45, CD 90, CD 117, CD 123, and CD 133.

In some embodiments, the target cell is from an autoimmune disease, such as, for example a neurological disorder (e.g., multiple sclerosis), a rheumatological disorder (e.g., rheumatoid arthritis, systemic sclerosis, systemic lupus), a hematological immunocytopenia (pure red cell aplasia, immune thrombopenia, pure white cell aplasia), or a gastrointestinal disorder (inflammatory bowel disease). In some embodiments, the neurological disorders include, for example, multiple sclerosis, myasthenia gravis, polyneuropathy, cerebellar degeneration, Guillain Barré syndrome, and amyotrophic lateral sclerosis. In some embodiments, rheumatological disorders include, for example, rheumatoid arthritis, systemic sclerosis, juvenile idiopathic arthritis, systemic lupus, erythematosus, dermatomyositis, mixed connective tissue disease, Bechet's disease, psoriatic arthritis, Ank. Spondylitis, Wegner's granulomatosis, and Cryoglobulinemia. In some embodiments, hematological immunocytopenias include, for example, immune thrombopenia, pure red cell aplasia, autoimmune hemolytic anemia, thrombotic thrombocytopenic purpura, Evan's syndrome, pancytopenia, and pure white cell aplasia.

In some embodiments, the target cells are memory T-cells, memory B-cells, and hematopoietic stem cells. In some embodiments, target cells are memory T-cells expressing antigens including, for example, CCR5, CCR7, CD11a, CD27, CD28, CD45RA, CD45RO, CD57, and/or CD62L. In some embodiments, the target cells are memory B-cells expressing antigens including, for example, CD 19, CD 21, CD 27, CD 40, and/or CD84. In some embodiments, the target cell is a hematopoietic stem cell expressing antigens including, for example, CD 34, CD 41, CD 45, CD 90, CD 117, CD 123, and CD 133. In some embodiments, the target cell is a hematopoietic stem cell expressing antigens, including, for example, CD13, CD33, CD 44, CD 47, CD 96, Mpl, Flt3, Esam1, Robo4, and/or TIM3.

In some embodiments, the target cells are senescent cells. In some embodiments, the target cells are senescent cells expressing antigens including, for example, DEP1, NTAL, EBP50, STX4, VAMP3, ARMX3, B2MG, LANCL1, VPS26A, or PLD3.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1. Control of T-Cell Effector Activity with a Smart-CAR

A Smart CAR is made using the third generation anti-CD20 CAR cassette described in Budde 2013 (Budde et al. PLoS1, 2013 doi:10.1371/journal.pone.0082742, which is hereby incorporated-by-reference in its entirety for all purposes), and the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the 3XL2bulge9 control device is engineered into the anti-CD20 CAR cassette in an appropriate expression vector.

This anti-CD20 Smart CAR is transfected by routine methods into T-cells (Jurkat cells and/or primary human T-cells), and stable populations of T-cells are selected using appropriate antibiotics (or other selection schemes). T-cell populations with anti-CD20 Smart CARs (CD20$^-$/CD22$^-$/CD3$^+$) are activated by co-incubation with anti-CD3/CD28 beads.

Activated anti-CD20 Smart CAR T-cells are co-cultured with CD20$^+$/CD22$^+$/CD3$^-$ Ramos target cells at Smart CAR T-cell:Ramos target ratios of 2:1, 5:1, and 10:1. Ligand for the RNA control device, theophylline is added to the culture medium at concentrations in the range of 500 µM to 1 mM (lower or greater concentrations can be used to titrate Smart-CAR activity to the desired level). The Smart-CAR T-cells and the Ramos cells are grown together for 48 hours. Cultures are washed, and then stained with anti-CD22 and anti-CD3 reagents, followed by counting of CD22$^+$ (Ramos target cells) and CD3$^+$ cells (Smart CAR T-cells). These measurements will identify the target cell killing rate (e.g., half-life) and the proliferation rate of the Smart-CAR T-cells at different levels of Smart-CAR expression.

Example 2. Control of T-Cell Effector Activity with Combination Smart-CARs in a Human Subject Nucleic acids encoding orthogonal Smart CARs that have specificity for distinct TAAs and respond to distinct small molecule ligands are constructed and are packaged into lentiviral vectors. Each of these Smart CARs demonstrate in vitro cytotoxic T-cell effector function and antigen-dependent expansion in response to cognate ligand exposure, and individually have known therapeutic windows in human patients.

To treat a human subject with tumors that express the defined set of multiple TAAs that are recognized by this Smart CAR pool, autologous T-cells are harvested from a patient's peripheral blood by apheresis and transduced ex vivo with lentivirus encoding the cognate Smart CARs, either individually or in pools. Expanded Smart CAR CD4+ and/or CD8+ T-cells are then adoptively transferred back into the patient. Each Smart CAR is individually activated with its own cognate small molecule ligand to initiate tumor recognition and elimination. As each Smart CAR is individually controlled, therapeutic windows for each Smart CAR are adjusted to enforce maximal graft vs. tumor response, with tolerable graft vs. host response. If the escape phase of tumor immunoediting is reached, the Smart CAR targeting the lost TAA is inactivated by removal of its cognate ligand to limit further graft vs. host response for a Smart CAR that no longer provides graft vs. tumor benefits. By controlling Smart CAR toxicity and parallelizing a distributed attack on TAAs quickly, durable remissions for any tumor type are achieved.

Example 3. Control of T-Cell Effector Activity with a DE-CAR

A DE-CAR is made using the anti-CD20 CAR cassette described in Budde 2013 (Budde et al. PLoS1, 2013 doi: 10.1371/journal.pone.0082742, which is hereby incorporated-by-reference in its entirety for all purposes), and the destabilizing element (DE) ecDHFR described in Iwamoto 2010 (Iwamoto et al. Chemistry and Biology, 2010 doi: 10.1016/j.chembiol.2010.07.009, which is hereby incorporated by reference in its entirety for all purposes). In an embodiment, the DE-CAR also encodes the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the DE of mutant scDHFR is engineered into the anti-CD20 CAR cassette in an appropriate expression vector. In an alternate embodiment, a nucleic acid encoding the 3XL2bulge9 control device is further engineered into the DE-anti-CD20 CAR cassette.

This anti-CD20 DE-CAR is transfected by routine methods into T-cells (Jurkat cells and/or primary human T-cells), and stable populations of T-cells are selected using appropriate antibiotics (or other selection schemes). T-cell populations with anti-CD20 DE-CARs or anti-CD20 Smart-DE-CARs (CD20$^-$/CD22$^-$/CD3$^+$) are activated by co-incubation with anti-CD3/CD28 beads.

Activated anti-CD20 DE-CAR T-cells or anti-CD20 Smart-DE-CAR T-cells are co-cultured with CD20$^+$/CD22$^+$/CD3$^-$ Ramos target cells at DE-CAR T-cell (or Smart-DE-CAR T-cell):Ramos target ratios of 2:1, 5:1, and 10:1. Ligand for the DE, trimethoprim, and/or ligand for the RNA control device, theophylline, is added to the culture medium at concentrations in the range of 500 µM to 1 mM (lower or greater concentrations can be used to titrate Smart-CAR activity to the desired level). The DE-CAR T-cells or Smart-DE-CAR T-cells and the Ramos cells are grown together for 48 hours. Cultures are washed, and then stained with anti-CD22 and anti-CD3 reagents, followed by counting of CD22$^+$ (Ramos target cells) and CD3$^+$ cells (DE-CAR and/or Smart-DE-CAR T-cells). These measurements will identify the target cell killing rate (e.g., half-life) and the proliferation rate of the Smart-CAR T-cells at different levels of Smart-CAR expression.

Example 4: Control of T-Cell Effector Activity with Combination DE-CARs and/or Smart-DE-CARs in a Human Subject Nucleic acids encoding orthogonal DE-CARs and/or Smart-DE-CARs that have specificity for distinct TAAs and respond to distinct small molecule ligands are constructed and are packaged into lentiviral vectors. Each of these DE-CARs and/or Smart-DE-CARs demonstrate in vitro cytotoxic T-cell effector function and antigen-dependent expansion in response to cognate ligand exposure, and individually have known therapeutic windows in human patients.

To treat a human subject with tumors that express the defined set of multiple TAAs that are recognized by this DE-CAR and/or Smart-DE-CAR pool, autologous T-cells are harvested from a patient's peripheral blood by apheresis and transduced ex vivo with lentivirus encoding the cognate DE-CARs and/or Smart-DE-CARs, either individually or in pools. Expanded DE-CAR and/or Smart-DE-CAR CD4+ and/or CD8+ T-cells are then adoptively transferred back into the patient. Each DE-CAR and/or Smart-DE-CAR is individually activated with its own cognate small molecule ligand(s) to initiate tumor recognition and elimination. As each DE-CAR and/or Smart-DE-CAR is individually controlled, therapeutic windows for each DE-CAR and/or Smart-DE-CAR is adjusted to enforce maximal graft vs. tumor response, with tolerable graft vs. host response. If the escape phase of tumor immunoediting is reached, the DE-CAR and/or Smart-DE-CAR targeting the lost TAA is inactivated by removal of its cognate ligand to limit further graft vs. host response for a DE-CAR and/or Smart-DE-CAR that no longer provides graft vs. tumor benefits. By controlling DE-CAR and/or Smart-DE-CAR toxicity and parallelizing a distributed attack on TAAs quickly, durable remissions for any tumor type are achieved.

Example 5: Integration of a Nucleic Acid Encoding a DE-CAR and/or Smart-DE-CAR at the CCR5 Locus of a Human T-Lymphocyte The CRISPR system is used to engineer human T-lymphocyte with a nucleic acid encoding a DE-CAR and/or Smart-DE-CAR of the invention downstream from an appropriate control region comprising, e.g., a promoter from SV40, CMV, UBC, EF1A, PGK or CAGG (Qin et al (2010) PLoS ONE. doi:10.1371/journal.pone.0010611, which is incorporated by reference in its entirety for all purposes), optionally a suitable enhancer, e.g., CMV early enhancer, and optionally other suitable regulatory sequences, e.g., woodchuck hepatitis B virus post-transcriptional regulatory element (WPRE; Donello, Loeb, and Hope (1998) Journal of Virology, which is incorporated by reference in its entirety for all purposes) translation initiator at short UTR (TISU; Elfakess et al (2011) NAR 39 (17): 7598-7609. doi:10.1093/nar/gkr484, which is incorporated by reference in its entirety for all purposes), A-U rich elements, beta-globin 3' UTR and poly-A sequence, SV40 3' UTR and poly-A sequence. This expression cassette is flanked on the 3' and 5' sides by appropriate CCR5 sequences for break point(s) associated with synthetic guide sequences obtained using the methodology of, for example, U.S. Pat. No. 8,697,359 (which is incorporated by reference in its entirety for all purposes).

Cas9 is introduced to the T-lymphocyte by electroporation of Cas9 mRNA, sgRNA, and donor nucleic acid encoding the DE-CAR and/or Smart-DE-CAR with appropriate control sequences and CCR5 flanking sequences paired to the sgRNA(s). (See, e.g., Qin et al., Genetics 115:176594 (2015); Qin et al., Genetics 115:176594 (2015), Kim et al (2014) Genome 1012-19, Kim et al. 2014 describe the Amaza Nucleofector, an optimized electroporation system, all three of these references are incorporated by reference in their entirety for all purposes.) Electroporated cells are deposited into multiwell plates and cultured in suitable media.

Representative cells are obtained and assayed by RFLP and/or sequencing to identify T-lymphocytes with DE-CAR and/or Smart-DE-CAR constructs integrated at the CCR5 locus.

Example 6: Identification of Antigen Binding Domains from a Subjects Antibody Repertoire A CAR chassis is made using the third generation anti-CD20 CAR cassette described in Budde 2013 (Budde et al. PLoS1, 2013 doi:10.1371/journal.pone.0082742, which is hereby incorporated-by-reference in its entirety for all purposes). This CAR construct is engineered to remove the anti-CD20 extracellular domain, and engineered to be an acceptor for cassettes of other antigen binding domains.

Antigen binding domains for the CAR chassis are made from the B-cells obtained from a subject who generated an effective immune response against a disease. For example, a patient who developed immunity to an infectious disease, such as a pandemic flu virus arising from influenza H5N1.

B-cells are obtained from the peripheral blood of the immune individual, and optionally, memory B-cells and/or plasma cells are obtained from the peripheral blood lymphocytes. cDNA is created from the mRNA of these cells, using primers and reaction conditions as disclosed, for example, in Coronella et al, Nucl. Acids Res. 28:e85 (2000), which is incorporated by reference in its entirety for all purpose. Alternatively, following the reverse transcription step, nucleic acids encoding expressed antibody genes may be amplified using other primer sets that are well-known in the art (e.g., those described above). Separate amplifications are performed to obtain nucleic acids encoding expressed heavy chains and expressed light chains. These pools of nucleic acids encoding heavy chains or light chains are combined in a combinatorial fashion to create a library of nucleic acids encoding single chain antibodies using, for example, the techniques and methods described in Pansri et al., BMC Biotechnol. 9:6 (2009); Peraldi-Roux, Methods Molc. Biol. 907:73-83 (2012), both of which are incorporated by reference in their entirety for all purposes.

The nucleic acids encoding the library of single chain antibodies are operably linked to nucleic acids encoding the CAR chassis described above. This creates a library of CARs with different antigen binding domains that represent the antibodies expressed in the immune individuals B-cells (or plasma cells and/or memory B-cells). This CAR library is transfected by routine methods into T-cells (Jurkat cells and/or primary human T-cells), and stable populations of T-cells are selected using appropriate antibiotics (or other selection schemes).

CAR T-cells are diluted to small or single numbers and placed in wells or containers and co-cultured with virus and/or viral infected cells at appropriate ratios. The Smart-CAR T-cells and the viral targets are grown together for 48-96 hours and, optionally, wells that show growth are diluted and the growth selection with viral targets is repeated for several rounds. After identification of clones that have CARs which proliferate in response to viral target, the antigen binding domains of these CARs and/or the CAR constructs can be isolated. The isolated antigen binding domains are further characterized for sequence and target affinity. The antigen binding domains are also used to make therapeutic antibodies for treating the infectious disease, and the CAR constructs can be used to make therapeutic T-cells for treating patients with the infectious disease.

Alternatively, the T-cells containing the CAR library as a whole are mixed with viral targets (virus or viral infected cells) and grown for 48-96 hours. T-cells with CARs that can bind to the viral target will be stimulated to proliferate, and those that don't react with the viral target should not grow or will grow only a small amount. In some embodiments, multiple rounds of selective growth with viral target may be performed to enrich and select for CAR clones that bind to the viral target. After several rounds of enrichment/selection, individual clones are obtained from the mixture and characterized for binding to the viral target. Again, clones of antigen binding domains can be used to make therapeutic antibodies for treating the infectious disease and the CAR constructs can be used or modified for use in treatment of the disease.

Example 7: Identification of Antigen Binding Domains Using FACs Sorting

A library of candidate antigen binding domains with CAR chassis is made according to Example 6. The host T-cells are engineered to include an optical reporter (e.g., GFP) operably linked to a NFAT control region so that reporter is expressed when the CAR construct is activated by binding of antigen. In this embodiment, T-cells with the CAR-antigen binding domain library are mixed with virus and/or viral infected cells and incubated for an appropriate amount of time (for GFP expression). T-cells with antigen binding domains that bind to virus or viral infected cell antigens are sorted from T-cells with nonbinding antigen binding domains using a Fluorescent Activated Cell Sorter.

In some embodiments, activation of T-cells with the CAR constructs is done through several cycles, optionally with increasing thresholds of GFP signal to screen for those antigen binding domains that have higher affinity for antigen.

Example 8: Identification of Antigen Binding Domains Using a Smart-CAR Chassis

In this example, the isolation of nucleic acids encoding antigen binding domains specific for an infectious disease described in Example 6 is repeated. These nucleic acids are operably linked to a Smart-CAR chassis made from the Smart CAR made in Example 1.

The RNA control device of the Smart CAR controls the amount of anti-infectious disease CAR made in the T-cell, and can be used to select for antigen binding domains with certain thresholds of binding affinity for the target antigen. In addition, the Smart CAR constructs that bind to the infectious disease agent can be used during therapy with CAR T-cells to control the activity of the CAR T-cells as they fight the infectious disease. Antigen binding domains identified and cloned from the enrichment/selection can also be used in antibody therapies for the treatment of the disease.

Example 9. Target Cell Killing Assay for a Chimeric Antigen Receptor Targeted to CD133 (AML)

A CAR is made using the anti-CD20 CAR cassette described in Budde 2013 (Budde et al. PLoS1, 2013 doi: 10.1371/journal.pone.0082742, which is hereby incorporated-by-reference in its entirety for all purposes), with the anti-CD133 mAb 293C3-SDIE is used for the extracellular element (Rothfelder et al., 2015, https://ash.confex.com/ash/2015/webprogram/Paper81121.html, which is incorporated by reference in its entirety for all purposes) replacing the anti-CD20 extracellular domain. In an embodiment, the anti-CD133 CAR also encodes the RNA control device, 3XL2bulge9 (Win and Smolke 2007 Proc. Natl Acad. Sci. 104 (36): 14283-88, which is hereby incorporated by reference in its entirety for all purposes), and/or the destabilizing element (DE) ecDHFR described in Iwamoto 2010 (Iwamoto et al. Chemistry and Biology, 2010 doi:10.1016/j.chembiol.2010.07.009, which is hereby incorporated by reference in its entirety for all purposes). A nucleic acid encoding the anti-CD20 CAR cassette is engineered to replace the anti-CD20 extracellular domain with the anti-CD133 element, and optionally the RNA control device and/or the destabilizing element are also engineered into the cassette. The anti-CD133 CAR with or without the RNA control device and/or the DE are cloned into appropriate expression vectors.

T-lymphocytes (Jurkat cells and/or primary human T-cells), or stable populations of T-cells are genetically modified using CRISPR/cas9 to make a double-allele knockout of FasL. Multiple guide RNAs specific for FasL are designed and then together with the cas9 enzyme are introduced into the T-cells. Double allele FasL knockouts are identified by T-lymphocyte clones that do not stain with anti-FasL antibody.

This anti-CD133 CAR, anti-CD133 DE-CAR, anti-CD133 Smart CAR, and/or the anti-CD133 DE-Smart CAR are transfected by routine methods into the double-allele knockout FasL T-cells. T-cell populations with anti-anti-CD133 CAR, anti-CD133 DE-CAR, anti-CD133 Smart CAR, and/or the anti-CD133 DE-Smart CAR (CD20$^-$/CD22$^-$/CD3$^+$) are activated by co-incubation with anti-CD3/CD28 beads.

CD133$^+$/CD3$^-$ AML target cells (e.g., U937, MV4-11, MOLM-14, HL-60 and/or KG1a) are genetically modified with the *Renilla* luciferase gene under the control of the CMV control region (pGL4.75 vector from Promega). The Rluc gene with CMV control region from pGL4.75 is engineered for insertion by CRISPR into genome of the AML target cells (e.g., U937, MV4-11, MOLM-14, HL-60 and/or KG1a). AML target cells that are Rluc+ are identified and used as target cells.

Activated anti-CD133 CAR, anti-CD133 DE-CAR, anti-CD133 Smart CAR, and/or the anti-CD133 DE-Smart CAR T-cells are co-cultured with the Rluc+, CD133$^+$/CD3$^-$ AML target cells (e.g., U937, MV4-11, MOLM-14, HL-60 and/or KG1a) at anti-CD133 CAR, anti-CD133 DE-CAR, anti-CD133 Smart CAR, and/or the anti-CD133 DE-Smart CAR T-cell:AML target ratios of 2:1, 5:1, and 10:1. Ligand for the DE, trimethoprim, and/or ligand for the RNA control device, theophylline, is added to the culture medium at concentrations in the range of 500 µM to 1 mM (lower or greater concentrations can be used to titrate Smart-CAR activity to the desired level). The anti-CD133 CAR, anti-CD133 DE-CAR, anti-CD133 Smart CAR, and/or the anti-CD133 DE-Smart CAR T-cells and the AML cells are grown together for 48 hours. Aliquots of the culture are washed, and then stained with anti-CD3 reagents, followed by counting of CD3$^+$ cells (anti-CD133 CAR, anti-CD133 DE-CAR, anti-CD133 Smart CAR, and/or the anti-CD133 DE-Smart CAR T-cells). Separate aliquots are placed in centrifuge tubes, spun to pellet the cells, and the supernatant is then tested for Rluc activity by adding appropriate reagents for the Rluc. Rluc activity is measured using an appropriate spectrophotometer. These measurements will identify the target cell killing rate (e.g., half-life) and the proliferation rate of the anti-CD133 CAR, anti-CD133 DE-CAR, anti-CD133 Smart CAR, and/or the anti-CD133 DE-Smart CAR T-cells at different levels of CAR and/or DE-CAR expression.

Example 10. Target Cell Killing Assay with Labeled Target Cells and Labeled Host Cells T-lymphocytes (Jurkat cells and/or primary human T-cells), or stable populations of T-cells are genetically modified using CRISPR/cas9 to make a double-allele knockout of FasL, and a double allele insertion at a safe harbor site of a nucleic acid encoding GFP under the control of a suitable promoter (e.g., CMV). Multiple guide RNAs specific for FasL and the safe harbor site/GFP construct are designed and then together with the cas9 enzyme are introduced into the T-cells. Double allele FasL knockouts are identified by T-lymphocyte clones that do not stain with anti-FasL antibody.

These FasL–, GFP+ T-lymphocytes are used as host cells for the anti-CD133 CAR described in Example 2. FasL–, GFP+ T-lymphocyte populations with anti-anti-CD133 CAR, anti-CD133 DE-CAR, anti-CD133 Smart CAR, and/ or the anti-CD133 DE-Smart CAR (CD20$^-$/CD22$^-$/CD3$^+$) are activated by co-incubation with anti-CD3/CD28 beads.

Activated anti-CD133 CAR, anti-CD133 DE-CAR, anti-CD133 Smart CAR, and/or the anti-CD133 DE-Smart CAR T-cells are co-cultured with the Rluc+, CD133$^+$/CD3$^-$ AML target cells of Example 2, under similar conditions to those of Example 2. After the appropriate incubation time, the host cells are measured by GFP fluorescence after excitation of GFP with 360-400 nm spectrum of light that excites GFP fluorescence. Target cell killing is measured by adding the appropriate reagents for Rluc and measuring the bioluminescence from the Rluc released from killed target cells.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for finding a CAR that is activated by an antigen, comprising the steps of: providing a plurality of eukaryotic cells wherein each eukaryotic cell comprises a nucleic acid wherein the nucleic acid comprises a polynucleotide encoding an antigen binding domain; a polynucleotide encoding a CAR chassis, wherein the CAR chassis is comprised of a transmembrane element and an intracellular element, wherein the transmembrane element is linked to the intracellular element, and wherein the polynucleotide encoding the antigen binding domain is operably linked to the polynucleotide encoding the CAR chassis, and wherein the plurality of eukaryotic cells collectively display a plurality of different antigen binding domains; mixing the antigen with the plurality of eukaryotic cells; incubating the plurality of eukaryotic cells with the antigen; and identifying a eukaryotic cell that is activated in the presence of the antigen, whereby the CAR that is activated by the antigen is identified.

2. The method of claim 1, further comprising the steps of: taking an aliquot of eukaryotic cells from the first incubation, mixing the aliquot of cells with the antigen, and incubating the eukaryotic cells with the antigen.

3. The method of claim 2, further comprising the steps of: taking an aliquot of eukaryotic cells from the second incubation, mixing the aliquot of cells with the antigen, and incubating the eukaryotic cells with the antigen.

4. The method of claim 1 wherein the polynucleotides encoding the antigen binding domains are derived from a plurality of nucleic acids obtained from a subject wherein the subject had an immune response to the antigen.

5. The method of claim 1, wherein the antigen is part of an infectious disease causing agent, and wherein the antigen mixed with the eukaryotic cell includes the infectious disease causing agent.

6. The method of claim 5, wherein the antigen is not known.

7. The method of claim 1, wherein the antigen is part of a cancer cell, and wherein the antigen mixed with the eukaryotic cell includes the cancer cell.

8. The method of claim 7, wherein the antigen is not known.

9. The method of claim 1, wherein the eukaryotic cell is a mammalian cell.

10. The method of claim 1, wherein the eukaryotic cell is a T-lymphocyte.

11. The method of claim 1, wherein the eukaryotic cell is a natural killer cell.

12. The method of claim 1, wherein the eukaryotic cell is a B-lymphocyte.

13. The method of claim 1, further comprising the steps of: obtaining a clone of the eukaryotic cell and the CAR that are activated by the antigen.

14. The method of claim 1, wherein the nucleic acid of claim 1 further comprises a polynucleotide encoding an RNA control device and wherein the polynucleotide encoding the RNA control device is operably linked to the polynucleotide encoding the CAR chassis.

15. The method of claim 1, wherein the nucleic acid of claim 1 further comprises a polynucleotide encoding a destabilizing element and wherein the polynucleotide encoding the destabilizing element is operably linked to the polynucleotide encoding the CAR chassis.

16. The method of claim 1, wherein the antigen binding domain is derived from an antibody.

17. The method of claim 16, wherein the antibody is a single chain antibody.

18. The method of claim 1, wherein the antigen binding domain is derived from a T-cell receptor.

19. The method of claim 18, wherein the T-cell receptor is a single chain T-cell receptor.

20. The method of claim 1, wherein the antigen binding domain is an innate immunity receptor.

* * * * *